US006147194A

United States Patent [19]
Collart et al.

[11] Patent Number: 6,147,194
[45] Date of Patent: Nov. 14, 2000

[54] EUKARYOTIC IMPDH POLYNUCLEOTIDE AND ANTIBODY COMPOSITIONS

[75] Inventors: Frank R. Collart, Bolingbrook; Eliezer Huberman, LaGrange, both of Ill.

[73] Assignee: Arch Development Corporation, Chicago, Ill.

[21] Appl. No.: 08/925,230

[22] Filed: Sep. 8, 1997

Related U.S. Application Data

[62] Division of application No. 07/232,302, Aug. 12, 1988, Pat. No. 5,665,583.
[51] Int. Cl.[7] ............................. C07K 16/00; C12N 9/64
[52] U.S. Cl. ................................... 530/387.1; 530/388.1; 530/387.7; 530/387.9; 530/388.8; 530/388.85; 530/389.1; 530/389.7; 530/388.26; 435/226
[58] Field of Search .............................. 530/387.1, 388.1, 530/387.7, 387.9, 388.8, 388.85, 389.1, 389.7, 388.26; 435/226

[56] References Cited

U.S. PATENT DOCUMENTS

| | | |
|---|---|---|
| 4,376,132 | 3/1983 | Eguchi et al. . |
| 4,399,216 | 8/1983 | Axel et al. . |
| 4,404,279 | 9/1983 | Ricotti et al. . |
| 4,423,147 | 12/1983 | Secher et al. . |
| 5,344,773 | 9/1994 | Wei et al. . |
| 5,665,583 | 9/1997 | Collart et al. . |

OTHER PUBLICATIONS

Goding J, Monoclonal Antibodies=Principles and Practice 1983 pp. 57–97.
Holmes E, et al., Biochimica et Biophysica Acta, 364 (1974) 209–217.
Anderson J and Sartorelli A, J Biolog Chem vol. 273, No. 18 Sep. 25, pp 1762–1768, 1968.
Atkins et al., "Purification and properties of inosine monophosphate oxidoreductase from nitrogen–fixing nodules of cowpea (Vigna unguiculata L. Walp)," *Arch. Biochem. Biophys.*, 236(2):807–814, 1985.
Boyum, "A one–stage procedure for isolation of granulocytes and lymphocytes from human blood: general sedimentation properties of white blood cells in a 1 g gravity field," *Scand. J. Clin. Lab. Invet.*, 21(97):51–55, 1968.
Caplan et al., "Introduction of genetic material into plant cells," *Science*, 222:815–821, 1983.
Chirgwin et al., "Isolation of biologically active ribonucleic acid from sources enriched in ribonuclease," *Biochem.*, 18(24):5294–5299, 1979.
Cohen and Sadee, "Contributions of the depletions of guanine and adenine nucleotides to the toxicity of purine starvation in the mouse T lymphoma cell line," *Cancer Res.*, 43:1587–1591, 1983.
Cohen et al., "Guanine nucleotide depletion and toxicity in mouse T lymphoma (S–49) cells," *J. Biol. Chem.*, 256(16):8713–8717, 1981.
Cohen, "Selection and characterization of mycophenolic acid–resistant leukemia cells," *Som. Cell Mol. Genet.*, 13(6):627–633, 1987.

Collart and Huberman, "Amplification of the IMP dehydrogenase gene in Chinese hamster cells resistant to mycophenolic acid," *Mol. Cell. Biol.*, 7(9):3328–3331, 1987.
Collart and Huberman, "Cloning and sequence analysis of the human and Chinese hamster inosine–5'–monophosphate dehydrogenase cDNAs," *J. Biol. Chem.*, 263(30):15769–15772, 1988.
Cooney et al., "A straightforward radiometric technique for measuring IMP dehydrogenase," *Anal. Biochem.*, 130:339–345, 1983.
Davis et al., "Calcium phosphate transfection of nonadherent and adherent cells with purified plasmids," In: *Basic Methods in Molecular Biology*, Section 18–1, pp. 286–289, 1986.
Devereux et al., "A comprehensive set of sequence analysis programs for the VAX," *Nucl. Acids Res.*, 12(1):387–395, 1984.
Duan and Sadée, "Distinct effects of adenine and guanine starvation on DNA synthesis associated with different pool sizes of nucleotide precursors," *Cancer Res.*, 47:4047–4051, 1987.
Elliott et al., "Differential expression of three α–tubulin genes in Chinese hamster ovary cells," *Mol. Cell. Biol.*, 5(1):236–241, 1985.
Feinberg and Vogelstein, "A technique for radiolabeling DNA restriction endonuclease fragments to high specific activity," *Anal. Biochem.*, 132:6–13, 1983.
Franklin and Cook, "The inhibition of nucleic acid synthesis by mycophenolic acid," *Biochem. J.*, 113:515–524, 1969.
Gilbert and Drabble, "Active–site modification of native and mutant forms of inosine–5'–monophosphate dehydrogenase from *Escherichia coli* K12," *Biochem. J.*, 191(2):533–541, 1980.
Gilbert et al., "Inosine 5'–monophosphate dehydrogenase of *Escherichia coli*," *Biochem. J.*, 183:481–494, 1979.
Heath et al., "Flavor potentiators,"In: *Flavor Chemistry and Technology*, AVI Publishing Co., Inc., Westport, CT, Ch. 9, pp. 318–331, 1986.

(List continued on next page.)

*Primary Examiner*—Albert Navarro
*Assistant Examiner*—Li Lee
*Attorney, Agent, or Firm*—Fulbright & Jaworski L.L.P

[57] ABSTRACT

Disclosed are purified and isolated DNA sequences encoding eukaryotic proteins possessing biological properties of inosine 5'-monophosphate dehydrogenase ("IMPDH"). Illustratively, mammalian (e.g., human) IMPDH-encoding DNA sequences are useful in transformation or transfection of host cells for the large scale recombinant production of the enzymatically active expression products and/or products (e.g., GMP) resulting from IMPDH catalyzed synthesis in cells. Vectors including IMPDH-encoding DNA sequences are useful in gene amplification procedures. Recombinant proteins and synthetic peptides provided by the invention are useful as immunological reagents and in the preparation of antibodies (including polyclonal and monoclonal antibodies) for quantitative detection of IMPDH.

13 Claims, 13 Drawing Sheets

OTHER PUBLICATIONS

Huberman et al., "Mutagen–induced resistance to mycophenolic acid in hamster cells can be associated with increased inosine 5'–phosphate dehydrogenase activity," *Proc. Natl. Acad. Sci. USA*, 78(5):3151–3154, 1981.

Hupe et al., "IMP dehydrogenase from the intracellular parasitic protozoan *Eimeria tenella* and its inhibition by mycophenolic acid," *J. Biol. Chem.*, 261(18):8363–8369, 1986.

Huynh et al., "Constructing and screening cDNA libraries in λgt10 and λgt11," In: *DNA Cloning: A Practical Approach*, IRL Press, Oxford; Washington D.C., Glover, ed., Chapter 2, vol. 1:49–78, 1985.

Ikegami et al., "Direct assay method for inosine 5'–monophosphate dehydrogenase activity," *J. Biochem.*, 150:155–160, 1985.

Ikegami et al., "Purification of IMP dehydrogenase from rat hepatoma 3924A," *Life Sci.*, 40(23):2277–2282, 1987.

Itakura et al., "Synthesis and use of synthetic oligonucleotides," *Ann. Rev. Biochem.*, 53:323–356, 1984.

Jackson et al., "Partial purification, properties and regulation of inosine 5'–phosphate dehydrogenase in normal and malignant rat tissues," *Biochem. J.*, 166:1–10, 1977.

Jackson and Weber, "IMP dehydrogenase, an enzyme linked with proliferation and malignancy," *Nature*, 256:331–333, 1975.

Joye et al., *Nucleic Acids Research*, 11(8):2325–2335, 1983.

Kittler et al., "A general immunochemical method for detecting proteins on blots," *Anal. Biochem.*, 137:210–216, 1984.

Klock and Bainton, "Degranulation and abnormal bactericidal function of granulocytes procured by reversible adhesion to nylon wool," *Blood*, 48(1):149–161, 1976.

Kozak, "Compilation and analysis of sequences upstream from the translational start site in eukaryotic mRNAs," *Nucl. Acids Res.*, 12(2):857–872, 1984.

Krishnaiah, "Inosinic acid 5'–monophosphate dehydrogenase of *Escherichia coli*: purification by affinity chromatography and some properties," *Arch. Biochem. Biophys.*, 170:567–575, 1975.

Laemmli, "Cleavage of structural proteins during the assembly of the head of bacteriophage T4," *Nature*, 227:680–685, 1970.

Maclean et al., "Introduction of novel genes into fish," *Biotech.*, 5:257–261, 1987.

Maniatis et al., In: *Molecular cloning: a laboratory manual*, Cold Spring Harbor Laboratory, NY, pp. 315–321, 1982.

Messing, "New vectors for cloning genes," *Meth. Enzymol.*, 101(2):20–78, 1983.

Miyagawa et al., "Cloning of the *Bacillus Subtilis* IMP dehydrogenase gene and its application to increased production of guanosine," *Biotech.*, 4:225–228, 1986.

Natsumeda et al., "Two distinct cDNAs for human IMP dehydrogenase," *J. Biol. Chem.*, 265(9);5292–5295, 1990.

Newman et al., "Activity of inosine monophosphate dehydrogenase inhibitors against human immunodeficiency virus," *Proc. Am. Assoc. Cancer Res. Meet.*, 28(0):323, 1987.

Nowack and Shaw, "Mycophenolic Acid Binding to Human Serum Albumin: Characterization and Relation to Pharmacodynamics," *Clin. Chem.*, 41(7):1011–1017, 1995.

Okado et al., "IMP dehydrogenase. II. Purification and properties of the enzyme from Yoshida sarcoma ascites tumor cells," *J. Biochem.*, 94:1605–1613, 1983.

Okayama and Berg, "A cDNA cloning vector that permits expression of cDNA inserts in mammalian cells," *Mol Cell Biol.*, 3(2):280–289, 1983.

Okayama and Berg, "High–efficiency cloning of full–length cDNA," *Mol. Cell. Biol.*, 2(2):161–170, 1982.

Old et al., "Cloning in Bacteria other than *E. coli*," In: *Principles of Gene Manipulation: An Introduction to Genetic Engineering*, Blackwell Scientific Publishers, 3rd ed., Chapter 8, pp. 10–13, 127–202, 288–293, 1985.

Palmiter et al., "Metallothionein–human GH fusion genes stimulate growth of mice," *Science*, 222:809–814, 1983.

Sambrook et al, "Using antibodies in immunological screening," In: *Molecular cloning: a laboratory manual*—2nd ed., Cold Spring Harbor Laboratory Press, 12.11–12.15, 1989.

Sanger et al., "DNA sequencing with chain–terminating inhibitors," *Proc. Natl. Acad. Sci. USA*, 74(12):5463–5467, 1977.

Schulz et al., "Optimizing the expression in *E. coli* of a synthetic gene encoding somatomedin–C (IGF–I)," *Mol. Biol. Chem.*, 13(6):1923–1939, 1985.

Sinkar et al., "ro1A locus of the Ri plasmid directs developmental abnormalities in transgenic tobacco plants," *Genes Devel.*, 2:688–697, 1988.

Tiedeman and Smith, "Isolation and sequence of a cDNA encoding mouse IMP dehydrogenase," *Gene*, 97:289–293, 1991.

Tiedeman and Smith, "Nucleotide sequence of the guaB locus encoding IMP dehydrogenase of *Escherichia coli* K12," *Nucleic Acids Res.*, 13(4):1303–1316, 1985.

Towbin et al., "Electrophoretic transfer of proteins from polyacrylamide gels to nitrocellulose sheets: procedure and some applications," *Proc. Natl. Acad. Sci. USA*, 76(9):4350–4354, 1979.

Tricot et al., "Hematological and biochemical action of tiazofurin (NSC 286193) in a case of refractory acute myeloid leukemia," *Cancer Res.*, 47:4988–4991, 1987.

Ullman, "Characterization of mutant lymphoma cells with altered inosinate dehydrogenase activities," *J. Biol. Chem.*, 258(1):523–5238, 1983.

Vaitukaitus, "Production of antisera with small doses of immunogen: multiple intradermal injections," *Meth. Enzymol.*, 73(Pt B):46–52, 1981.

Weber, "Biochemical strategy of cancer cells and the design of chemotherapy: G.H.A. Clowes Memorial Lecture," *Cancer Res.*, 43:3466–3492, 1983.

Weber et al., "Biochemical commitment to replication in cancer cells," *Adv. Enzyme Regul.*, 18:3–26, 1980.

Yamada et al., "Action of the active metabolites of tiazofurin and ribavirin on purified IMP dehydrogenase," *Biochem.*, 27:2193–2196, 1988.

Zassenhaus et al., "Rapid electroelution of nucleic acids from agarose and acrylamide gels," *Anal. Biochem.*, 125:125–130, 1982.

```
  1  GGGCGGTCCTCGGAGACACGGCGGCGGTGTCCTGTGTTGGCCATGGCCGACTACCTGATTA   60
                                   M  A  D  Y  L  I  S

61  GTGGGGCAGTCCTACGTGCCAGAGACGGACTCACAGCACAGCTCTTCAACTGCG        120
      G  G  T  S  Y  V  P  D  D  G  L  T  A  Q  Q  L  F  N  C  G

121  GAGACGGCCTCACCTACAATGACTTTCTCATTCCCTGGGTACATGACTTCACTGCAG     180
      D  G  L  T  Y  N  D  F  L  I  P  G  Y  I  D  F  T  A  D

181  ACCAGGTGGACCTGACTTCTGCTCTGACCAAGAAAATCACTCTTAAGACCCCACTGGTTT  240
      Q  V  D  L  T  S  A  L  T  K  K  I  T  L  K  T  P  L  V  S

241  CCTCTCCCATGGACACAGTCACAGAGGCTGGGATGGCCATAGCAATGGCGCTTACAGGCG  300
      S  P  M  D  T  V  T  E  A  G  M  A  I  A  M  A  L  T  G  G

301  GTATTGGCTTCATCCACCACAACTGTACACCTGAATTCCAGGCCAATGAAGTTCGGAAAG  360
      I  G  F  I  H  H  N  C  T  P  E  F  Q  A  N  E  V  R  K  V

361  TGAAGAAATATGAACAGGGATTCATCACAGACCCTGTGGTCCTCAGCCCCAAGGATCGCG  420
      K  K  Y  E  Q  G  F  I  T  D  P  V  V  L  S  P  K  D  R  V
```

FIG. 1A

```
421  TGCGGGATGTGTTTTGAGGCCAAGGCCCGGCATGGTTTCTGCGGTATCCCAATCACAGACA  480
      R  D  V  F  E  A  K  A  R  H  G  F  C  G  I  P  I  T  D  T

481  CAGGCCGGATGGGGAGCCGCTTGGTGTGGCATCATCTCCTCCAGGACATTGATTTTCTCA  540
      G  R  M  G  S  R  L  V  G  I  I  S  S  R  D  I  D  F  L  K

541  AAGAGGAGGAACATGACTGTTTCTTGGAAGAGATAATGACAAAGAGGGAAGACTTGGTGG  600
      E  E  H  D  C  F  L  E  E  I  M  T  K  R  E  D  L  V  V

601  TAGCCCCCGCAGCATCACACTGAAGGAGGCAAATGAATTCTGCAGCGCAGCAAGAAGG  660
      A  P  R  S  I  T  L  K  E  A  N  E  I  L  Q  R  S  K  K  G

661  GAAAGTTGCCCATTGTAAATGAAGATGATGAGCTTGTGGCCATCATTGCCCGGACAGACC  720
      K  L  P  I  V  N  E  D  D  E  L  V  A  I  I  A  R  T  D  L

721  TGAAGAAGAATCGGGACTACCCACTAGCCTCCAAAGATGCCAAGAAACAGCTGCTGTGTG  780
      K  K  N  R  D  Y  P  L  A  S  K  D  A  K  K  Q  L  L  C  G

781  GGGCAGCCATTGGCACTCATGAGGATGACAAGTATAGGCTGGACTTGCTCGCCCAGGCTG  840
      A  I  G  T  H  E  D  D  K  Y  R  L  D  L  L  A  Q  A  G
```

FIG. 1B

```
841   GTGTGGATGTAGTGGTTTTGGACTCTCTTCCCAGGGAAATTCCATCTTCCCAGATCAATATGA   900
      V  V  D  V  V  V  L  D  S  S  Q  G  N  S  I  F  Q  I  N  M  I
901   TCAAGTACATCAAAGACAAATACCCTAATCTCCAAGTCATTGGAGGCAATGTGGTCACTG     960
      K  Y  I  K  D  K  Y  P  N  L  Q  V  I  G  G  N  V  V  T  A
961   CTGCCCAGGCCAAGAACCTCATTGATGCAGGTGTGGATGCCCTGCGGGTGGGCATGGGAA    1020
      A  Q  A  K  N  L  I  D  A  G  V  D  A  L  R  V  G  M  G  S
1021  GTGGCTCCATCTGCATTACGCAGGAAGTGCTGGCCTGTGGGCGCCCAAGCAACAGCAG     1080
      G  S  I  C  I  T  Q  E  V  L  A  C  G  R  P  Q  A  T  A  V
1081  TGTACAAGGTGTCAGAGTATGCACGGCGCTTTGGTGTTCCGGTCATTGCTGATGGAGGAA   1140
      Y  K  V  S  E  Y  A  R  R  F  G  V  P  V  I  A  D  G  G  I
1141  TCCAAAAATGTGGGTCATATTGCGAAAGCCCTTGGCCCTCCACAGTCATGATGG        1200
      Q  N  V  G  H  I  A  K  A  L  A  L  G  A  S  T  V  M  M  G
1201  GCTCTCCTCCTGGCTGCCACCACTGAGGCCCCCTGAGGCCCCCTGGTGAATACTTCTTTTCCGATGGGATCC  1260
      S  L  L  A  A  T  T  E  A  P  G  E  Y  F  F  S  D  G  I  R
```

FIG. 1C

```
1261  GGCTAAAGAAATATCGCGGTATGGGTTCTCTCGATGCCATGGACAAGCACCTCAGCAGCC  1320
       L   K   K   Y   R   G   M   G   S   L   D   A   M   D   K   H   L   S   S   Q

1321  AGAACAGATATTCAGTGAAGCTGACAAAATCAAAGTGGCCCAGGGAGTGTCTGGTGCTG  1380
       N   R   Y   F   S   E   A   D   K   I   K   V   A   Q   G   V   S   G   A   V

1381  TGCAGGACAAAGGGTCAATCCACAAATTTGTCCCTTACCTGATTGCTGGCATCCAACACT  1440
       C   Q   D   K   G   S   I   H   K   F   V   P   Y   L   I   A   G   I   Q   H   S

1441  CATGCCCAGGACATTGGTGCCAAGAGCTTGACCCAAGTCCGAGCCATGATGTACTCTGGGG  1500
       C   Q   D   I   G   A   K   S   L   T   Q   V   R   A   M   M   Y   S   G   E

1501  AGCTTAAGTTTGAGAAGAGAACGTCCTCAGCCCAGGTGGAAGGTGGCGTCCATAGCCCTCC  1560
       L   K   F   E   K   R   T   S   S   A   Q   V   E   G   G   V   H   S   L   H

1561  ATTCGTATGAGAAGCGGCTTTTCTGAAAAGGGATCCAGCACACCTCCTCGGTTTTTTTTT  1620
       S   Y   E   K   R   L   F

1621  CAATAAAAGTTTAGAAAGACCC  1642
```

FIG. 1D

Chinese hamster IMP dehydrogenase cDNA sequence and translation, clone CIMP

```
1   CACGGCGTCCGTGCTCCTCGTTGGCCATGGCGGACTACCTGATTAGCGGGAGGCACATCTTA   60
                      M  A  D  Y  L  I  S  G  G  T  S  Y

61  CGTGCCCGACGACGGGCTCACAGCGCAGCAGCTCTTCAACTGCGGGGATGGCCTCACCTA   120
     V  P  D  D  G  L  T  A  Q  Q  L  F  N  C  G  D  G  L  T  Y

121 CAACGATTTTCTCATTCTTCCTGGGTATATCGACTTCACTGCCGACCAAGTGGATTTGAC   180
     N  D  F  L  I  L  P  G  Y  I  D  F  T  A  D  Q  V  D  L  T

181 CTCTGCTCTAACTAAGAAGATCACCCTGAAGACCCCACTGGTTTCCTCACCTATGGACAC   240
     S  A  L  T  K  K  I  T  L  K  T  P  L  V  S  S  P  M  D  T

241 TGTCACAGAGGCTGGAATGGCCATTGCAATGGCGCTTACAGGAGGTATTGGCTTCATCCA   300
     V  T  E  A  G  M  A  I  A  M  A  L  T  G  G  I  G  F  I  H

301 CCACAACTGTACACCTGAATTCCAGGCCAATGAACTTCGGAAAGTAAAGAAATATGAACA   360
     H  N  C  T  P  E  F  Q  A  N  E  V  R  K  V  K  K  Y  E  Q
```

FIG. 2A

```
361  GGGATTCATAACTGATCCTGTAGTCCTTAGCCCCAAGGATCGTGTGAGGGATGTTTTTGA    420
      G  F  I  T  D  P  V  V  L  S  P  K  D  R  V  R  D  V  F  E

421  AGCCAAAGCCAGGCATGGCTTCTGTGTTATCCCCATCACAGATACAGGCCGATGGGGAG     480
      A  K  A  R  H  G  F  C  G  I  P  I  T  D  T  G  R  M  G  S

481  TCGACTGGTGTGGGCATCATTTCTTCAAGGGATATATTGATTTTCTCAAGGAGGAAGAGCATGA  540
      R  L  V  G  I  I  S  R  D  I  D  F  L  K  E  E  E  H  D

541  CCGTTTCTTGGAGGAGATCATGACAAAGAGGGAAGATTTGGTGGTGGCCCCTGCAGGCAT    600
      R  F  L  E  E  I  M  T  K  R  E  D  L  V  V  A  P  A  G  I

601  CACTCTGAAGGAGGCAAATGAAATTCTGCAGCGCAGTAAAAAGGGAAAGTTGCCCATTGT    660
      T  L  K  E  A  N  E  I  L  Q  R  S  K  K  G  K  L  P  I  V

661  GAATGAAAATGATGAGCTGGTAGCCATCATTGCTCGGACAGACCTGAAGAAGAATCGTGA    720
      N  E  N  D  E  L  V  A  I  I  A  R  T  D  L  K  K  N  R  D

721  TTACCCCATTGGCTTCCAAAGATGCCAAAAAGCAGCTACTATGTGGGCAGCCATTGGTAC   780
      Y  P  L  A  S  K  D  A  K  K  Q  L  L  C  G  A  A  I  G  T
```

FIG. 2B

```
 781   TCATGAGGATGACAAGTATAGGCTGGACTTACTGGCTCTTGCTGGTGTGGATGTAGTGGT   840
       H   E   D   D   K   Y   R   L   D   L   L   A   L   A   G   V   D   V   V   V

841   TTTGGACTCTTCCCAGGGAAACTCCATTTTCCAAATCAATATGATCAAATACATGAAAGA   900
       L   D   S   S   Q   G   N   S   I   F   Q   I   N   M   I   K   Y   M   K   E

901   GAAATACCCCAATCTCCAAGTCATTGGAGGCAATGTAGTCACTGCTGCTCAAGCCAAGAA   960
       K   Y   P   N   L   Q   V   I   G   G   N   V   V   T   A   A   Q   A   K   N

961   CCTCATAGACGCCAGGTGTGGATGCTCTGCGAGTTGGCATGGGGTGTGGTTCCATCTGCAT   1020
       L   I   D   A   G   V   D   A   L   R   V   G   M   G   C   G   S   I   C   I

1021   TACTCAGGAAGTGTTGGCTGTGGCCTGTGTCGGCCCCAAGCAACAGCAGTGTACAAGGTTTCTGA   1080
       T   Q   E   V   L   A   C   G   R   P   Q   A   T   A   V   Y   K   V   S   E

1081   GTATGCTCGGCGCTTTGGTGTGTTCCTGTTATTGCTGATGGAGGAATCCAAAATGTGGGTCA   1140
       Y   A   R   R   F   G   V   P   V   I   A   D   G   G   I   Q   N   V   G   H

1141   TATTGCCAAAGCTTTGGCTCTTGGAGCTTCTACAGTCATGATGGGCTCCCTCTTGGCTGC   1200
       I   A   K   A   L   A   L   G   A   S   T   V   M   M   G   S   L   L   A   A
```

FIG. 2C

```
1201 CACCACCGAAGCCCCTGGTGAGTACTTCTTCTCAGATGGGATCCGGCTAAAAAAGTACCG  1260
      T  T  E  A  P  G  E  Y  F  F  S  D  G  I  R  L  K  K  Y  R

1261 TGGTATGGGTTCTCTTGATGCCATGGACAAGCATCTCAGCAGCCAGAACCGATATTTCAG  1320
      G  M  G  S  L  D  A  M  D  K  H  L  S  S  Q  N  R  Y  F  S

1321 TGAAGCTGACAAAATCAAAGTGGCCCAAGGAGTTTCAGGAGCTGTGCAGGACAAAGGGTC  1380
      E  A  D  K  I  K  V  A  Q  G  V  S  G  A  V  Q  D  K  G  S

1381 TATCCACAAGTTCGTCCCTTATTTGATTGCTGGCATCCAGCATTCCTGTCAGGACATTGG  1440
      I  H  K  F  V  P  Y  L  I  A  G  I  Q  H  S  C  Q  D  I  G

1441 TGCCAAGAGTTTAACCCAAGTCAGAGAGCCATGATGTACTCTGGGGAACTCAAGTTTGAGAA  1500
      A  K  S  L  T  Q  V  R  A  M  M  Y  S  G  E  L  K  F  E  K

1501 GAGAACATCCTCAGCTCAGGTGGAAGGTGGTGTCCACAGCCTTCATTCGTATGAGAAGCG  1560
      R  T  S  S  A  Q  V  E  G  G  V  H  S  L  H  S  Y  E  K  R

1561 GCTTTTCTGAAAAGAGATCCAGTATATGCCTTGAATTTTTCAATAAAAGTTTTGAAAAAA  1620
      L  F
```

FIG. 2D

MOUSE IMP DEHYDROGENASE, SEQUENCE MI1.

```
    1 CGCCCCAAGGATCGTGTACGCGATGTTTTGAGGCCAAAGCCAGGCATGGCTTCTGTGGT   60
      ------+---------+---------+---------+---------+---------+
      GCGGGGTTCCTAGCACATGCGCTACAAAAACTCCGGTTTCGGTCCGTACCGAAGACACCA

61 ATCCCCATCACAGATACAGGCCGATGGGGAGTCGATTGGTGGGCATCATCTCCTCAAGG  120
      ------+---------+---------+---------+---------+---------+
      TAGGGGTAGTGTCTATGTCCGGCTACCCCTCAGCTAACCACCCGTAGTAGAGGAGTTCC

121 GACATTGATTTCCTCAAGGAGGAAGAGCATGACCGGTTCTTGGAAGAGATCATGACTAAG  180
      ------+---------+---------+---------+---------+---------+
      CTGTAACTAAAGGAGTTCCTCCTTCTCGTACTGGCCAAGAACCTTCTCTAGTACTGATTC

181 AGGGAAGATTTGGTGGTCGCCCCTGCGCCCCGGGCGTCACTCTGAAAGAGGCAAATGAGATTCTG  240
      ------+---------+---------+---------+---------+---------+
      TCCCTTCTAAACCACCAGCGGGGACGCGGCCGCAGTGAGACTTTCTCCGTTTACTCTAAGAC

241 CAGCGAAGTAAAAAGGGAAAGTTGCCCATTGTGAATGAAAATGATGAGCTGGTAGCCATC  300
      ------+---------+---------+---------+---------+---------+
      GTCGCTTCATTTTTCCCTTTCAACGGGTAACACTTACTTTTACTACTCGACCATCGGTAG

301 ATTGCCCGGACAGACCTAAAGAAGAATCGTGATTACCCCCTGGC                  344
      ------+---------+---------+---------+-----
      TAACGGGCCTGTCTGGATTTCTTCTTAGCACTAATGGGGACCG
```

FIG. 3A

MOUSE IMP DEHYDROGENASE, SEQUENCE MI2.

```
1    CGGACCCACATTTGGATTCCTCCATCAGCAATAACAGGAACACCAAAGCGACGGGCATA    60
     ---------+---------+---------+---------+---------+---------+
     GCCTGGGTGTAAACCTAAGGAGGTAGTCGTTATTGTCCTTGTGGTTTCGCTGCCCGTAT

61   CTCAGAGACCTTGTACACTGCTGTGGCTTGGGCCGCCACAGGCCAACACTTCCTGGGT    120
     ---------+---------+---------+---------+---------+---------+
     GAGTCTCTGGAACATGTGACGACACCGAACCCCGGGTGTCCGGTTGTGAAGGACCCA

121  GATGCAGATGGAACCACTTCCCATGCCGCAAAGCATCTACACCTGCATCTATGAG      180
     ---------+---------+---------+---------+---------+---------+
     CTACGTCTACCTTGGTGAAGGGTACGGCTGAGCGTTTCGTAGATGTGGACGTAGATACTC

181  GTTCTTGGCTTGCGCAGCAGGTGACTACATTGCCTCCAATGACCTGTAGACTGGGATACT  240
     ---------+---------+---------+---------+---------+---------+
     CAAGAACCGAACGCGTCGTCCACTGATGTAACGGAGGTTACTGGACATCTGACCCTATGA
```

FIG. 3B

```
241  TCTCCTTGATGTATTTGATCATATTGATTTGGAAGATGGAGTTTCCCTGGAAGAGTCCA
     ----+----+----+----+----+----+----+----+----+----+----+----+  300
     AGAGGAACTACATAAACTAGTATAACTAAACCTTCTACCTCAAAGGGACCCTTCTCAGGT

301  AAACCACTACATCCACACCAGCAAGGGCCAGTAAGTCAGCCTATACTTGTCATCCTTCAT
     ----+----+----+----+----+----+----+----+----+----+----+----+  360
     TTTGGTGATGTAGGTGTGGTCGTTCCCGGTCATTCAGTCGGATATGAACAGTAGGAAGTA

361  GAGTGCCAATGGCTGCCCACACAGCAGTTGCTT
     ----+----+----+----+----+----+---  393
     CTCACGGTTACCGACGGGTGTGTCGTCAACGAA
```

FIG. 3C

```
human     1    MADYLISGGTSYVPDDGLTAQQLFNCGDGLTYNDFLILPGYIDFTADQVDLTSALTKKIT
hamster        MADYLISGGTSYVPDDGLTAQQLFNCGDGLTYNDFLILPGYIDFTADQVDLTSALTKKIT 61    LKTPLVSSPMDTVTEAGMAIAMALTGGIGFIHHNCTPEFQANEVRKVKKYEQGFITDPVV                    60
               LKTPLVSSPMDTVTEAGMAIAMALTGGIGFIHHNCTPEFQANEVRKVKKYEQGFITDPVV                   120

121    LSPKDRVRDVFEAKARHGFCGIPITDTGRMGSRLVGIISSRDIDFLKEEEHD[C]FLEEIMT
               LSPKDRVRDVFEAKARHGFCGIPITDTGRMGSRLVGIISSRDIDFLKEEEHD[R]FLEEIMT               180

181    KREDLVVAP[RS]ITLKEANEILQRSKKGKLPIVNE[DD]ELVAIIARTDLKKNRDYPLASKDA
                         *  *                        *
               KREDLVVAP[AG]ITLKEANEILQRSKKGKLPIVNE[ND]ELVAIIARTDLKKNRDYPLASKDA            240

241    KKQLLCGAAIGTHEDDKYRLDLLA[Q]AGVDVVVLDSSQGNSIFQINMIKYI[K]KYPNLQVI
                                       *                              * *
               KKQLLCGAAIGTHEDDKYRLDLLA[L]AGVDVVVLDSSQGNSIFQINMIKYM[EK]YPNLQVI            300
```

FIG. 4A

```
301  GGNVVTAAQAKNLIDAGVDALRVGMGSGSICITQEVLACGRPQATAVYKVSEYARRFGVP     360
     GGNVVTAAQAKNLIDAGVDALRVGMGCGSICITQEVLACGRPQATAVYKVSEYARRFGVP
                              *

361  VIADGGIQNVGHIAKALALGASTVMMGSLLAATTEAPGEYFFSDGIRLKKYRGMGSLDAM     420
     VIADGGIQNVGHIAKALALGASTVMMGSLLAATTEAPGEYFFSDGIRLKKYRGMGSLDAM

421  DKHLSSQNRYFSEADKIKVAQGVSGAVQDKGSIHKFVPYLIAGIQHSCQDIGAKSLTQVR     480
     DKHLSSQNRYFSEADKIKVAQGVSGAVQDKGSIHKFVPYLIAGIQHSCQDIGAKSLTQVR

481  AMMYSGELKFEKRTSSAQVEGGVHSLHSYEKRLF     514
     AMMYSGELKFEKRTSSAQVEGGVHSLHSYEKRLF
```

FIG. 4B

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1642 base pairs
      (B) TYPE: nucleic acid
      (C) STRANDEDNESS: single
      (D) TOPOLOGY: linear (xi) SEQUENCE DESCRIPTION: SEQ ID NO:1:

```
GGGCGGTCCT CGGAGACACG CGGCGGTGTC CTGTGTTGGC CATGGCCGAC TACCTGATTA      60

GTGGGGGCAC GTCCTACGTG CCAGACGACG GACTCACAGC ACAGCAGCTC TTCAACTGCG     120

GAGACGGCCT CACCTACAAT GACTTTCTCA TTCTCCCTGG GTACATCGAC TTCACTGCAG     180

ACCAGGTGGA CCTGACTTCT GCTCTGACCA AGAAAATCAC TCTTAAGACC CCACTGGTTT     240

CCTCTCCCAT GGACACAGTC ACAGAGGCTG GGATGGCCAT AGCAATGGCG CTTACAGGCG     300

GTATTGGCTT CATCCACCAC AACTGTACAC CTGAATTCCA GGCCAATGAA GTTCGGAAAG     360

TGAAGAAATA TGAACAGGGA TTCATCACAG ACCCTGTGGT CCTCAGCCCC AAGGATCGCG     420

TGCGGGATGT TTTTGAGGCC AAGGCCCGGC ATGGTTTCTG CGGTATCCCA ATCACAGACA     480

CAGGCCGGAT GGGGAGCCGC TTGGTGGGCA TCATCTCCTC CAGGGACATT GATTTTCTCA     540

AGAGGAGGA ACATGACTGT TTCTTGGAAG AGATAATGAC AAAGAGGGAA GACTTGGTGG      600

TAGCCCCCCG CAGCATCACA CTGAAGGAGG CAAATGAAAT TCTGCAGCGC AGCAAGAAGG     660

GAAAGTTGCC CATTGTAAAT GAAGATGATG AGCTTGTGGC CATCATTGCC CGGACAGACC     720

TGAAGAAGAA TCGGGACTAC CCACTAGCCT CCAAAGATGC CAAGAAACAG CTGCTGTGTG     780

GGGCAGCCAT TGGCACTCAT GAGGATGACA AGTATAGGCT GGACTTGCTC GCCCAGGCTG     840

GTGTGGATGT AGTGGTTTTG GACTCTTCCC AGGGAAATTC CATCTTCCAG ATCAATATGA     900

TCAAGTACAT CAAAGACAAA TACCCTAATC TCCAAGTCAT TGGAGGCAAT GTGGTCACTG     960

CTGCCCAGGC CAAGAACCTC ATTGATGCAG GTGTGGATGC CCTGCGGGTG GGCATGGGAA    1020

GTGGCTCCAT CTGCATTACG CAGGAAGTGC TGGCCTGTGG GCGGCCCCAA GCAACAGCAG    1080

TGTACAAGGT GTCAGAGTAT GCACGGCGCT TTGGTGTTCC GGTCATTGCT GATGGAGGAA    1140

TCCAAAATGT GGGTCATATT GCGAAAGCCT TGGCCCTTGG GGCCTCCACA GTCATGATGG    1200

GCTCTCTCCT GGCTGCCACC ACTGAGGCCC CTGGTGAATA CTTCTTTTCC GATGGGATCC    1260

GGCTAAAGAA ATATCGCGGT ATGGGTTCTC TCGATGCCAT GGACAAGCAC CTCAGCAGCC    1320

AGAACAGATA TTTCAGTGAA GCTGACAAAA TCAAAGTGGC CCAGGGAGTG TCTGGTGCTG    1380

TGCAGGACAA AGGGTCAATC CACAAATTTG TCCCTTACCT GATTGCTGGC ATCCAACACT    1440

CATGCCAGGA CATTGGTGCC AAGAGCTTGA CCCAAGTCCG AGCCATGATG TACTCTGGGG    1500

AGCTTAAGTT TGAAGAGAGA ACGTCCTCAG CCCAGGTGGA AGGTGGCGTC CATAGCCTCC    1560

ATTCGTATGA GAAGCGGCTT TTCTGAAAAG GGATCCAGCA CACCTCCTCG GTTTTTTTTT    1620

CAATAAAAGT TTAGAAAGAC CC                                            1642
```

(2) INFORMATION FOR SEQ ID NO:2:

(i) SEQUENCE CHARACTERISTICS:
        (A) LENGTH: 1620 base pairs
        (B) TYPE: nucleic acid
        (C) STRANDEDNESS: single
        (D) TOPOLOGY: linear (xi) SEQUENCE DESCRIPTION: SEQ ID NO:2:

```
CACGCGTCCG TGCTCCTCGT TGGCCATGGC GGACTACCTG ATTAGCGGAG GCACATCTTA      60
CGTGCCCGAC GACGGGCTCA CAGCGCAGCA GCTCTTCAAC TGCGGGATG GCCTCACCTA      120
CAACGATTTT CTCATTCTTC CTGGGTATAT CGACTTCACT GCCGACCAAG TGGATTTGAC     180
CTCTGCTCTA ACTAAGAAGA TCACCCTGAA GACCCCACTG GTTTCCTCAC CTATGGACAC     240
TGTCACAGAG GCTGGAATGG CCATTGCAAT GGCGCTTACA GGAGGTATTG GCTTCATCCA     300
CCACAACTGT ACACCTGAAT TCCAGGCCAA TGAAGTTCGG AAAGTAAAGA AATATGAACA     360
GGGATTCATA ACTGATCCTG TAGTCCTTAG CCCCAAGGAT CGTGTGAGGG ATGTTTTTGA     420
AGCCAAAGCC AGGCATGGCT TCTGTGGTAT CCCCATCACA GATACAGGCC GGATGGGGAG     480
TCGACTGGTG GGCATCATTT CTTCAAGGGA TATTGATTTT CTCAAGGAGG AAGAGCATGA     540
CCGTTTCTTG GAGGAGATCA TGACAAAGAG GGAAGATTTG GTGGTGGCCC CTGCAGGCAT     600
CACTCTGAAG GAGGCAAATG AAATTCTGCA GCGCAGTAAA AAGGGAAAGT TGCCCATTGT     660
GAATGAAAAT GATGAGCTGG TAGCCATCAT TGCTCGGACA GACCTGAAGA AGAATCGTGA     720
TTACCCATTG GCTTCCAAAG ATGCCAAAAA GCAGCTACTA TGTGGGGCAG CCATTGGTAC     780
TCATGAGGAT GACAAGTATA GGCTGGACTT ACTGGCTCTT GCTGGTGTGG ATGTAGTGGT     840
TTTGGACTCT TCCCAGGGAA ACTCCATTTT CCAAATCAAT ATGATCAAAT ACATGAAAGA     900
GAAATACCCC AATCTCCAAG TCATTGGAGG CAATGTAGTC ACTGCTGCTC AAGCCAAGAA     960
CCTCATAGAC GCAGGTGTGG ATGCTCTGCG AGTTGGCATG GGGTGTGGTT CCATCTGCAT    1020
TACTCAGGAA GTGTTGGCCT GTGGTCGGCC CCAAGCAACA GCAGTGTACA AGGTTTCTGA    1080
GTATGCTCGG CGCTTTGGTG TTCCTGTTAT TGCTGATGGA GGAATCCAAA ATGTGGGTCA    1140
TATTGCCAAA GCTTTGGCTC TTGGAGCTTC TACAGTCATG ATGGGCTCCC TCTTGGCTGC    1200
CACCACCGAA GCCCCTGGTG AGTACTTCTT CTCAGATGGG ATCCGGCTAA AAAAGTACCG    1260
TGGTATGGGT TCTCTTGATG CCATGGACAA GCATCTCAGC AGCCAGAACC GATATTTCAG    1320
TGAAGCTGAC AAAATCAAAG TGGCCCAAGG AGTTTCAGGA GCTGTGCAGG ACAAAGGGTC    1380
TATCCACAAG TTCGTCCCTT ATTTGATTGC TGGCATCCAG CATTCCTGTC AGGACATTGG    1440
TGCCAAGAGT TTAACCCAAG TCAGAGCCAT GATGTACTCT GGGGAACTCA AGTTTGAGAA    1500
GAGAACATCC TCAGCTCAGG TGGAAGGTGG TGTCCACAGC CTTCATTCGT ATGAGAAGCG    1560
GCTTTTCTGA AAAGAGATCC AGTATATGCC TTGAATTTTT CAATAAAAGT TTTGAAAAAA    1620
```

(2) INFORMATION FOR SEQ ID NO:3:

(i) SEQUENCE CHARACTERISTICS:
        (A) LENGTH: 344 base pairs
        (B) TYPE: nucleic acid
        (C) STRANDEDNESS: double
        (D) TOPOLOGY: linear (ix) FEATURE:
        (A) NAME/KEY: misc_feature
        (B) LOCATION: 1..344
        (D) OTHER INFORMATION: /note= "This sequence is the top strand of a double stranded sequence. The sequence immediately
following is the bottom strand of the double stranded sequence."

(xi) SEQUENCE DESCRIPTION: SEQ ID NO:3:

```
CGCCCCAAGG ATCGTGTACG CGATGTTTTT GAGGCCAAAG CCAGGCATGG CTTCTGTGGT      60

ATCCCCATCA CAGATACAGG CCGGATGGGG AGTCGATTGG TGGGCATCAT CTCCTCAAGG     120

GACATTGATT TCCTCAAGGA GGAAGAGCAT GACCGGTTCT TGGAAGAGAT CATGACTAAG     180

AGGGAAGATT TGGTGGTCGC CCCTGCCGGC GTCACTCTGA AGAGGCAAA TGAGATTCTG      240

CAGCGAAGTA AAAAGGGAAA GTTGCCCATT GTGAATGAAA ATGATGAGCT GGTAGCCATC     300

ATTGCCCGGA CAGACCTAAA GAAGAATCGT GATTACCCCC TGGC                     344
```

(2) INFORMATION FOR SEQ ID NO:4:

(i) SEQUENCE CHARACTERISTICS:
  (A) LENGTH: 344 base pairs
  (B) TYPE: nucleic acid
  (C) STRANDEDNESS: double
  (D) TOPOLOGY: linear (ix) FEATURE:
  (A) NAME/KEY: misc_feature
  (B) LOCATION: 1..344
  (D) OTHER INFORMATION: /note= "This sequence is the bottom
   strand of a double stranded sequence, read from 5' to 3'. The
   top strand with which it belongs is the sequence immediately
   preceding it in this listing."

(xi) SEQUENCE DESCRIPTION: SEQ ID NO:4:

```
GCCAGGGGGT AATCACGATT CTTCTTTAGG TCTGTCCGGG CAATGATGGC TACCAGCTCA      60

TCATTTTCAT TCACAATGGG CAACTTTCCC TTTTTACTTC GCTGCAGAAT CTCATTTGCC     120

TCTTTCAGAG TGACGCCGGC AGGGGCGACC ACCAAATCTT CCCTCTTAGT CATGATCTCT     180

TCCAAGAACC GGTCATGCTC TTCCTCCTTG AGGAAATCAA TGTCCCTTGA GGAGATGATG     240

CCCACCAATC GACTCCCCAT CCGGCCTGTA TCTGTGATGG GGATACCACA GAAGCCATGC     300

CTGGCTTTGG CCTCAAAAAC ATCGCGTACA CGATCCTTGG GGCG                     344
```

(2) INFORMATION FOR SEQ ID NO:5:

(i) SEQUENCE CHARACTERISTICS:
  (A) LENGTH: 393 base pairs
  (B) TYPE: nucleic acid
  (C) STRANDEDNESS: double
  (D) TOPOLOGY: linear (ix) FEATURE:
  (A) NAME/KEY: misc_feature
  (B) LOCATION: 1..393
  (D) OTHER INFORMATION: /note= "This sequence is the top
   strand of a double stranded sequence. The sequence immediately
   following is the bottom strand of the double stranded sequence."

(xi) SEQUENCE DESCRIPTION: SEQ ID NO:5:

```
CGGACCCACA TTTTGGATTC CTCCATCAGC AATAACAGGA ACACCAAAGC GACGGGCATA      60

CTCAGAGACC TTGTACACTG CTGTGGCTTG GGGCCGCCCA CAGGCCAACA CTTCCTGGGT     120

GATGCAGATG GAACCACTTC CCATGCCGAC TCGCAAAGCA TCTACACCTG CATCTATGAG     180

GTTCTTGGCT TGCGCAGCAG GTGACTACAT TGCCTCCAAT GACCTGTAGA CTGGGATACT     240

TCTCCTTGAT GTATTTGATC ATATTGATTT GGAAGATGGA GTTTCCCTGG AAGAGTCCA      300

AAACCACTAC ATCCACACCA GCAAGGGCCA GTAAGTCAGC CTATACTTGT CATCCTTCAT     360

GAGTGCCAAT GGCTGCCCAC ACAGCAGTTG CTT                                  393
```

(2) INFORMATION FOR SEQ ID NO:6:

(i) SEQUENCE CHARACTERISTICS:
        (A) LENGTH: 393 base pairs
        (B) TYPE: nucleic acid
        (C) STRANDEDNESS: double
        (D) TOPOLOGY: linear (ix) FEATURE:
        (A) NAME/KEY: misc_feature
        (B) LOCATION: 1..393
        (D) OTHER INFORMATION: /note= "This sequence is the bottom
            strand of a double stranded sequence, read from 5' to 3'.  The
            top strand with which it belongs is the sequence immediately
            preceding it in this listing."

(xi) SEQUENCE DESCRIPTION: SEQ ID NO:6:

```
AAGCAACTGC TGTGTGGGCA GCCATTGGCA CTCATGAAGG ATGACAAGTA TAGGCTGACT    60

TACTGGCCCT TGCTGGTGTG GATGTAGTGG TTTTGGACTC TTCCCAGGGA AACTCCATCT   120

TCCAAATCAA TATGATCAAA TACATCAAGG AGAAGTATCC CAGTCTACAG GTCATTGGAG   180

GCAATGTAGT CACCTGCTGC GCAAGCCAAG AACCTCATAG ATGCAGGTGT AGATGCTTTG   240

CGAGTCGGCA TGGGAAGTGG TTCCATCTGC ATCACCCAGG AAGTGTTGGC CTGTGGGCGG   300

CCCCAAGCCA CAGCAGTGTA CAAGGTCTCT GAGTATGCCC GTCGCTTTGG TGTTCCTGTT   360

ATTGCTGATG GAGGAATCCA AAATGTGGGT CCG                                393
```

(2) INFORMATION FOR SEQ ID NO:7:

(i) SEQUENCE CHARACTERISTICS:
        (A) LENGTH: 514 amino acids
        (B) TYPE: amino acid
        (C) STRANDEDNESS:
        (D) TOPOLOGY: linear (xi) SEQUENCE DESCRIPTION: SEQ ID NO:7:

```
Met Ala Asp Tyr Leu Ile Ser Gly Gly Thr Ser Tyr Val Pro Asp Asp
1               5                   10                  15

Gly Leu Thr Ala Gln Gln Leu Phe Asn Cys Gly Asp Gly Leu Thr Tyr
                20                  25                  30

Asn Asp Phe Leu Ile Leu Pro Gly Tyr Ile Asp Phe Thr Ala Asp Gln
            35                  40                  45

Val Asp Leu Thr Ser Ala Leu Thr Lys Lys Ile Thr Leu Lys Thr Pro
    50                  55                  60

Leu Val Ser Ser Pro Met Asp Thr Val Thr Glu Ala Gly Met Ala Ile
65                  70                  75                  80

Ala Met Ala Leu Thr Gly Gly Ile Gly Phe Ile His His Asn Cys Thr
                85                  90                  95

Pro Glu Phe Gln Ala Asn Glu Val Arg Lys Val Lys Lys Tyr Glu Gln
            100                 105                 110

Gly Phe Ile Thr Asp Pro Val Val Leu Ser Pro Lys Asp Arg Val Arg
        115                 120                 125

Asp Val Phe Glu Ala Lys Ala Arg His Gly Phe Cys Gly Ile Pro Ile
    130                 135                 140

Thr Asp Thr Gly Arg Met Gly Ser Arg Leu Val Gly Ile Ile Ser Ser
145                 150                 155                 160

Arg Asp Ile Asp Phe Leu Lys Glu Glu His Asp Cys Phe Leu Glu
                165                 170                 175

Glu Ile Met Thr Lys Arg Glu Asp Leu Val Val Ala Pro Arg Ser Ile
```

-continued

```
                180               185               190
Thr Leu Lys Glu Ala Asn Glu Ile Leu Gln Arg Ser Lys Lys Gly Lys
        195               200               205

Leu Pro Ile Val Asn Glu Asp Glu Leu Val Ala Ile Ile Ala Arg
    210               215               220

Thr Asp Leu Lys Lys Asn Arg Asp Tyr Pro Leu Ala Ser Lys Asp Ala
225               230               235               240

Lys Lys Gln Leu Leu Cys Gly Ala Ala Ile Gly Thr His Glu Asp Asp
            245               250               255

Lys Tyr Arg Leu Asp Leu Leu Ala Gln Ala Gly Val Asp Val Val
            260               265               270

Leu Asp Ser Ser Gln Gly Asn Ser Ile Phe Gln Ile Asn Met Ile Lys
            275               280               285

Tyr Ile Lys Asp Lys Tyr Pro Asn Leu Gln Val Ile Gly Gly Asn Val
        290               295               300

Val Thr Ala Ala Gln Ala Lys Asn Leu Ile Asp Ala Gly Val Asp Ala
305               310               315               320

Leu Arg Val Gly Met Gly Ser Gly Ser Ile Cys Ile Thr Gln Glu Val
                325               330               335

Leu Ala Cys Gly Arg Pro Gln Ala Thr Ala Val Tyr Lys Val Ser Glu
            340               345               350

Tyr Ala Arg Arg Phe Gly Val Pro Val Ile Ala Asp Gly Gly Ile Gln
            355               360               365

Asn Val Gly His Ile Ala Lys Ala Leu Ala Leu Gly Ala Ser Thr Val
            370               375               380

Met Met Gly Ser Leu Leu Ala Ala Thr Thr Glu Ala Pro Gly Glu Tyr
385               390               395               400

Phe Phe Ser Asp Gly Ile Arg Leu Lys Lys Tyr Arg Gly Met Gly Ser
                405               410               415

Leu Asp Ala Met Asp Lys His Leu Ser Ser Gln Asn Arg Tyr Phe Ser
            420               425               430

Glu Ala Asp Lys Ile Lys Val Ala Gln Gly Val Ser Gly Ala Val Gln
            435               440               445

Asp Lys Gly Ser Ile His Lys Phe Val Pro Tyr Leu Ile Ala Gly Ile
    450               455               460

Gln His Ser Cys Gln Asp Ile Gly Ala Lys Ser Leu Thr Gln Val Arg
465               470               475               480

Ala Met Met Tyr Ser Gly Glu Leu Lys Phe Glu Lys Arg Thr Ser Ser
                485               490               495

Ala Gln Val Glu Gly Gly Val His Ser Leu His Ser Tyr Glu Lys Arg
            500               505               510

Leu Phe (2) INFORMATION FOR SEQ ID NO:8:

(i) SEQUENCE CHARACTERISTICS:
        (A) LENGTH: 514 amino acids
        (B) TYPE: amino acid
        (C) STRANDEDNESS:
        (D) TOPOLOGY: linear (xi) SEQUENCE DESCRIPTION: SEQ ID NO:8:

Met Ala Asp Tyr Leu Ile Ser Gly Gly Thr Ser Tyr Val Pro Asp Asp
1               5               10              15

Gly Leu Thr Ala Gln Gln Leu Phe Asn Cys Gly Asp Gly Leu Thr Tyr
```

-continued

```
            20                  25                  30
Asn Asp Phe Leu Ile Leu Pro Gly Tyr Ile Asp Phe Thr Ala Asp Gln
                35                  40                  45

Val Asp Leu Thr Ser Ala Leu Thr Lys Lys Ile Thr Leu Lys Thr Pro
 50                  55                  60

Leu Val Ser Ser Pro Met Asp Thr Val Thr Glu Ala Gly Met Ala Ile
 65                  70                  75                  80

Ala Met Ala Leu Thr Gly Gly Ile Gly Phe Ile His His Asn Cys Thr
                85                  90                  95

Pro Glu Phe Gln Ala Asn Glu Val Arg Lys Val Lys Lys Tyr Glu Gln
                    100                 105                 110

Gly Phe Ile Thr Asp Pro Val Val Leu Ser Pro Lys Asp Arg Val Arg
                115                 120                 125

Asp Val Phe Glu Ala Lys Ala Arg His Gly Phe Cys Gly Ile Pro Ile
                130                 135                 140

Thr Asp Thr Gly Arg Met Gly Ser Arg Leu Val Gly Ile Ile Ser Ser
145                 150                 155                 160

Arg Asp Ile Asp Phe Leu Lys Glu Glu His Asp Arg Phe Leu Glu
                165                 170                 175

Glu Ile Met Thr Lys Arg Glu Asp Leu Val Val Ala Pro Ala Gly Ile
                180                 185                 190

Thr Leu Lys Glu Ala Asn Glu Ile Leu Gln Arg Ser Lys Lys Gly Lys
                195                 200                 205

Leu Pro Ile Val Asn Glu Asn Asp Glu Leu Val Ala Ile Ile Ala Arg
                210                 215                 220

Thr Asp Leu Lys Lys Asn Arg Asp Tyr Pro Leu Ala Ser Lys Asp Ala
225                 230                 235                 240

Lys Lys Gln Leu Leu Cys Gly Ala Ala Ile Gly Thr His Glu Asp Asp
                245                 250                 255

Lys Tyr Arg Leu Asp Leu Leu Ala Leu Ala Gly Val Asp Val Val Val
                260                 265                 270

Leu Asp Ser Ser Gln Gly Asn Ser Ile Phe Gln Ile Asn Met Ile Lys
                275                 280                 285

Tyr Met Lys Glu Lys Tyr Pro Asn Leu Gln Val Ile Gly Gly Asn Val
                290                 295                 300

Val Thr Ala Ala Gln Ala Lys Asn Leu Ile Asp Ala Gly Val Asp Ala
305                 310                 315                 320

Leu Arg Val Gly Met Gly Cys Gly Ser Ile Cys Ile Thr Gln Glu Val
                325                 330                 335

Leu Ala Cys Gly Arg Pro Gln Ala Thr Ala Val Tyr Lys Val Ser Glu
                340                 345                 350

Tyr Ala Arg Arg Phe Gly Val Pro Val Ile Ala Asp Gly Gly Ile Gln
                355                 360                 365

Asn Val Gly His Ile Ala Lys Ala Leu Ala Leu Gly Ala Ser Thr Val
                370                 375                 380

Met Met Gly Ser Leu Leu Ala Ala Thr Thr Glu Ala Pro Gly Glu Tyr
385                 390                 395                 400

Phe Phe Ser Asp Gly Ile Arg Leu Lys Lys Tyr Arg Gly Met Gly Ser
                405                 410                 415

Leu Asp Ala Met Asp Lys His Leu Ser Ser Gln Asn Arg Tyr Phe Ser
                420                 425                 430

Glu Ala Asp Lys Ile Lys Val Ala Gln Gly Val Ser Gly Ala Val Gln
                435                 440                 445
```

-continued

```
Asp Lys Gly Ser Ile His Lys Phe Val Pro Tyr Leu Ile Ala Gly Ile
    450                 455                 460

Gln His Ser Cys Gln Asp Ile Gly Ala Lys Ser Leu Thr Gln Val Arg
465                 470                 475                 480

Ala Met Met Tyr Ser Gly Glu Leu Lys Phe Glu Lys Arg Thr Ser Ser
                485                 490                 495

Ala Gln Val Glu Gly Gly Val His Ser Leu His Ser Tyr Glu Lys Arg
            500                 505                 510

Leu Phe
```

EUKARYOTIC IMPDH POLYNUCLEOTIDE AND ANTIBODY COMPOSITIONS

This is a divisional of application Ser. No. 07/232,302 filed Aug. 12, 1988, which issued as U.S. Pat. No. 5,665,583 on Sep. 9, 1997.

BACKGROUND OF THE INVENTION

The present invention relates generally to inosine 5'-monophosphate dehydrogenase (IMPDH) and more particularly to purified and isolated DNA sequences that encode proteins possessing the biological properties of eukaryotic IMPDH, to the expression products of these DNA sequences in transformed or transfected host cells, to recombinant and synthetic proteins and peptides having amino acid sequences based on the sequence of amino acids deduced from these DNA sequences, to antibodies specific for such proteins and peptides, to analytical procedures for the detection and quantification of such peptides and proteins and nucleic acids related thereto, to the use of IMPDH-encoding DNA sequences as selectable markers and as tools for gene amplification in recombinant hosts, and to cell lines and organisms displaying enhanced production of IMPDH and/or elevated levels of products such as guanosine monophosphate (GMP), whose synthesis in cells is dependent on the activity of IMPDH.

The enzyme IMPDH (EC 1.2.1.14) catalyzes the formation of xanthine monophosphate (XMP) from inosine monophosphate (IMP). In the purine de novo synthetic pathway, IMPDH is positioned at the branch point in the synthesis of adenine and guanine nucleotides and is thus the rate-limiting enzyme in the de novo synthesis of guanine nucleotides, such as guanosine 5-monophosphate. [Weber, *Cancer Res.*, 43:3466–3492 (1983); Weber, et al., *Adv. Enzyme Regul.*, 18:3–26 (1980)]. Inhibition of cellular IMPDH activity results in an abrupt cessation of DNA synthesis [Franklin, et al., *Biochem. J.*, 113:515–524 (1969); Cohen, et al., *J. Biol. Chem.*, 256:8713–8717 (1981); and Duan, et al., *Cancer Res.*, 47:4047–4051 (1987)] and a cell cycle block at the G1-S interface [Cohen, et al., *Cancer Res.*, 43:1587–1591 (1983)]. Because IMPDH is essential in providing the necessary precursors for DNA and RNA biosynthesis, normal tissues that exhibit increased cell proliferation generally exhibit increased IMPDH activity [Jackson, et al., *Nature*, 256:331–333 (1975); Jackson, et al., *Biochem. J.*, 166:1–10 (1977), Cooney, et al., *Anal. Biochem.*, 130:339–345 (1983)]. Similarly, increased cell proliferation is accompanied by elevated enzyme activity in certain rat hepatomas with varied growth rates. Weber, *Cancer Res.*, 43:3466–3492 (1983). These hepatomas manifest IMPDH activities that are disproportionately higher than those of normal tissues, suggesting that IMPDH is associated with cell proliferation and may be linked to either malignant cell transformation or tumor progression.

To investigate the role of IMPDH in growth regulation and malignancy, attempts have been made to purify the enzyme to homogeneity to allow preparation of specific antibodies thereto and to isolate IMPDH-encoding DNA.

IMPDH isolated from bacterial sources has been determined to vary widely with respect to allosteric properties, size, and subunit composition. IMPDH isolated from *E. coli* has been purified and characterized as a tetramer of identical subunits [Gilbert, et al., *Biochem. J.*, 183:481–494 (1979); and Krishnaiah, *Arch. Biochem. Biophys.*, 170:567–575 (1975)]. Unlike mammalian cell enzymes, the *E. coli* IMPDH enzyme is reported to be insensitive to the inhibitory effect of mycophenolic acid [Franklin, et al., *Biochem. J.*, 113:515–524 (1969)]. In *E. coli*, IMPDH has been determined to be the product of the guaB locus and the sequence of the guaB structural gene and surrounding DNA has been determined to span 1.533 kb and to code for an IMPDH subunit sequence of 511 amino acids with a calculated molecular weight 54,512 [Tiedeman, et al., *Nucleic Acids Research*, 13:1303 (1985)].

Miyagawa, et al., *Bio/Tech.*, 4:225 (1986), have described the cloning of the *Bacillus subtilis* IMPDH gene, which, upon re-introduction into a *B. subtilis* strain that overproduced inosine, resulted in an increased production of guanosine, accompanied by a decreased accumulation of inosine. The IMPDH gene was localized on a 6.5 kb insert and further localized to a Hind III-partially digested 2.9 kb fragment. However, the gene was not reported to have been isolated and no information was provided with respect to the DNA sequence of the gene.

While a number of workers have reported the purification or partial purification of IMPDH from a variety of eukaryotic cell sources, including ascites cells, thymus cells, mouse LS cells, and other mammalian cells, none have been successful in obtaining substantial information about the amino acid sequence of the IMPDH protein, or in establishing the utility of anti-IMPDH antibodies in the characterization of the cellular role of IMPDH.

Eukaryotic IMPDH has been obtained from one plant and several animal species, including cowpea nodule cells [Atkins, et al., *Arch. Biochem. Biophys.*, 236:807–814 (1985)], Yoshida sarcoma ascites cells [Okada, et al., *J. Biochem.*, 94:1605–1613 (1983)], rat hepatoma 3924A cells [Ikegami, et al., *Life Sci.*, 40:2277–2282 (1987) and Yamada, et al., *Biochem.*, 27:2193–2196 (1988)] and Chinese hamster cells [Collart, et al., *Mol. Cell. Biol.*, 7:3328–3331 (1987)]. The disclosures of the last-mentioned publication by the present inventors are specifically incorporated by reference herein. In all of these reports, denaturing polyacrylamide gel electrophoresis was used to assess purity and to estimate molecular weight. The reported molecular weight for all of the above metioned enzymes was approximately 56,000. A polyclonal antibody raised against the purified protein was prepared for the enzyme isolated from Yoshida sarcoma ascites cells, rat hepatoma 3924A cells, and Chinese hamster cells. As described in detail, infra, only in the case of the antibody prepared against the Chinese hamster enzyme was an antibody determined to be useful in examination of cellular regulation and useful in isolation of eukaryotic IMPDH-encoding DNA.

There continues to exist a need in the art for information regarding IMPDH enzymes of eukaryotic origins (especially of vertebrate and more particularly of mammalian origins) such as can be provided by the isolation, sequencing, and recombinant system utilization of DNA sequences encoding the same. The availability of such materials and information would make possible a vast array of novel systems and methodologies based thereon including methods and materials useful in production of products displaying IMPDH activity.

BRIEF SUMMARY OF THE INVENTION

The present invention provides novel purified and isolated DNA sequences encoding eukaryotic inosine 5'-monophosphate dehydrogenase (IMPDH), which have allowed for the initial determination of the primary structural conformation (i.e., amino acid sequence) of the eukaryotic protein. Specifically provided are sequences encoding human, mouse, and Chinese hamster IMPDH. Provided also are alternate DNA forms such as genomic DNA and DNA manufactured by partial or total chemical synthesis from nucleotides. The association of DNA sequences of the invention with expression regulatory DNA sequences, such as promoters, enhancers and the like, allows for in vivo and in vitro transcription to form messenger RNA, which, in turn, is subject to translation to provide IMPDH protein in large quantities.

Among the multiple aspects of the present invention, therefore, is the provision of (a) novel eukaryotic IMPDH DNA sequences as set out in FIG. 1A, FIG. 1B, FIG. 1C, FIG. 1D, FIG. 2A, FIG. 2B, FIG. 2C, FIG. 2D, FIG. 3A, FIG. 3B, and FIG. 3C; (b) IMPDH-encoding DNA sequences, which hybridize thereto under hybridization conditions of the stringency equal to or greater than the conditions described herein as used in the initial isolation of cDNAs of the invention, which also encode proteins with IMPDH biological activities; and (c) DNA sequences encoding the same, allelic variant and/or analog IMPDH proteins, which incorporate, at least in part, degenerate codons. Correspondingly provided are viral or circular plasmid DNA vectors incorporating such DNA sequences and prokaryotic and eukaryotic host cells transformed or transfected with such DNA sequences and vectors, as well as novel methods for the recombinant production of IMPDH proteins through cultured growth of such hosts and isolation thereof from the hosts or from their culture media.

According to another of its aspects, cell lines and organisms having enhanced production of IMPDH, as well as enhanced production of guanosine monophosphate (GMP), are also provided. Preferred embodiments of such cells include the transformed or transfected host cells described initially above. Also comprehended are naturally occurring or mutagenized eukaryotic cells, which are selected for increased IMPDH production (e.g., on the basis of capacity for growth in the presence of elevated levels of cytotoxic IMPDH inhibitors) and then additionally subjected to stepwise incremental selection in the presence of a cytotoxic IMPDH inhibitor such as mycophenolic acid (MPA), ribavirin, brenidin, and tiazofurin. Illustratively, naturally occurring or mutagenized cells capable of growing in medium containing 0.1 to 0.5 µg/mL MPA are subjected to stepwise selection at increasingly higher levels of the agent.

The preparation and incorporation of IMPDH DNA sequences for use as a selectable marker to select for cells that have incorporated a selected fragment of foreign DNA into their genetic material is also embraced by the present invention. In one illustration of the DNA selection systems of the invention, Chinese hamster IMPDH encoding DNA is operatively associated in a plasmid construct with appropriate expression control sequences, and e.g., a DNA sequence coding for the *E. coli* gpt protein. This plasmid construct is then introduced into hamster cells, and cells functionally incorporating the IMPDH/gpt gene construct are selected on the basis of survival in culture media that contains MPA.

Novel protein products of the invention include recombinant-produced compounds having the primary structural conformation (i.e., amino acid sequence) of IMPDH protein, as well as peptide fragments thereof and synthetic peptides assembled to be duplicative of amino acid sequences thereof. Proteins, protein fragments, and synthetic peptides of the invention are projected to have numerous uses including therapeutic, diagnostic and prognostic uses and also provide the basis for the preparation of monoclonal and polyclonal antibodies specifically immunoreactive with IMPDH. Preferred protein fragments and synthetic peptides include those that duplicate continuous antigenic epitope sequences of the full-length protein.

Preferred protein products of the invention include approximately 56 kDa IMPDH peptides having the deduced sequence of 514 amino acid residues for human and Chinese hamster proteins set out in FIG. 1A, FIG. 1B, FIG. 1C, FIG. 1D, FIG. 2A, FIG. 2B, FIG. 2C, and FIG. 2D. The preferred 56 kDa IMPDH polypeptide is characterized by a capacity to specifically bind IMP with a $K_i$ equal to approximately 25 µmol, a sensitivity to inhibition by IMPDH inhibitors such as mycophenolic acid, and immunoprecipitability by rabbit anti-IMPDH antisera.

Antibodies specific for the novel peptide products of the invention preferably bind with high immunospecificity to IMPDH protein, fragments, and peptides, recognizing epitopes that are not common to other proteins.

Also provided by the present invention are novel procedures for the detection and/or quantification of the IMPDH protein, as well as the corresponding nucleic acids, e.g., DNA and mRNA, associated therewith. Antibodies of the invention may be used in known immunological procedures for quantitative detection of IMPDH protein in fluid and tissue samples. DNA sequences of the invention may be suitably labeled and used for the quantitative detection of mRNA encoding IMPDH or assessment of any genetic alteration resulting in amplification or rearrangement of the IMPDH gene.

Other aspects and advantages of the present invention will be apparent upon consideration of the following detailed description thereof, which includes illustrative examples of the practice of the invention, reference being made to the drawing wherein:

FIG. 1A, FIG. 1B, FIG 1C, and FIG. 1D set forth the base sequence of a human species IMPDH cDNA (SEQ ID NO: 1) and the deduced amino acid sequence (SEQ ID NO: 7) of the protein product of expression of the sequence;

FIG. 2A, FIG. 2B, FIG. 2C, and FIG. 2D set forth the base sequence of a Chinese hamster species IMPDH cDNA (SEQ ID NO: 2) and the deduced amino acid sequence (SEQ ID NO: 8) of the expression product thereof;

FIGS. 3A, 3b and 3c set forth the base sequence for 737 bases of the 750 bases of a mouse species cDNA (SEQ ID NO:3, SEQ ID NO:4, SEQ ID NO:5, and SEQ ID NO:6) fragment; and, FIG. 4A and 4B provide a comparison of the human and Chinese hamster species IMPDH deduced amino acid sequences.

DETAILED DESCRIPTION

The following examples operate to illustrate practice of the invention in its numerous aspects. More particularly, Example 1 relates to the to the generation of cultured cell variants displaying altered levels of IMPDH activity as a result of mutagenesis and incremental selection. Example 2 relates to IMPDH purification from Chinese hamster cells and the partial purification of IMPDH from human cells. Example 3 relates to the preparation of rabbit anti-IMPDH antiserum, the isolation of IMPDH-specific IgG, and the use of this IgG in immunoblot analysis. Example 4 relates to the isolation and characterization of IMPDH cDNA from a mouse bone marrow library, a Chinese hamster library, and a human cDNA library. Example 5 relates to the protease digestion and amino terminal sequencing of the purified Chinese hamster IMPDH protein. Example 6 relates to the use of an IMPDH DNA construct as a selectable marker.

Example 7 relates to the analysis of IMPDH expression in normal and in malignant cells.

The examples that follow are for illustrative purposes only and are not intended in any way to limit the scope of the invention.

EXAMPLE 1

Generation of Cell Variants with Altered IMPDH Activity

To investigate the control of IMPDH enzyme in mammalian cells, cell variants were generated from the Chinese hamster V79 line of cells according to the general procedures of Huberman, et al., *Proc. Nat'l. Acad. Sci. (USA)*, 78:3151–54 (1981).

To generate MPA-resistant cells, $4 \times 10^6$ 2-day-old exponentially growing V79 cells cultured in 100-mm Petri dishes were treated with the chemical mutagen/carcinogen N-methyl-N'-nitro-N-nitrosoguanidine (MNNG). After 3 hours of treatment, both the control and the MNNG-treated cells were dissociated with trypsin ethylenediaminetetraacetic acid (EDTA) solution and seeded at $10^5$ cells per 100-mm Petri dish. Unless otherwise noted, the cells were dissociated 6 days later and reseeded at 200 cells per 60-mm dish in 5 mL of medium for the determination of cloning efficiency and at $2 \times 10^4$ cells per 60-mm dish in 4 mL of medium for the determination of the number of MPA-resistant cells. Two days later, MPA was added in 1 mL of medium to give a final concentration of 1 µg/mL. Thus, an expression time of 8 days was used for the selection of MPA resistance. Cloning efficiency was determined by counting the number of Giemsa-stained colonies of six to eight dishes per point at 7–8 days after cell seeding; the number of MPA-resistant cell variants was determined by counting Giemsa-stained colonies in 40 Petri dishes per point at 18–21 days after cell seeding. The frequency of the drug-resistant colonies was calculated per $10^5$ colony-forming cells based on the cloning efficiency and the number of cells seeded for mutant selection.

In addition, after a 6-day expression time, a sample of control and MNNG-treated (0.5 µg/mL) cells was incubated with MPA at 0, 0.1, and 0.3 µg/mL. Both the control and MNNG-treated cells had a similar growth rate, yielding, after 5 days of growth, means (±SD) of $5.0 \pm 0.3$, $1.4 \pm 0.2$, and $0.2 \pm 0.05 \times 10^6$ cells per Petri dish for MPA at 0, 0.1, and 0.3 µg/mL, respectively. These results indicate that control and MNNG-treated cells exhibit not only a similar growth rate but also a similar susceptibility to the cytotoxic effect of MPA.

According to the present invention, the resistance level of one of these cell variants was further increased by a stepwise selection in the presence of increasing concentrations of MPA. After adaptation to the higher concentration of MPA, the cells were seeded in medium containing an increased concentration of MPA at 200 cells per 60-mm petri dish, and MPA-resistant colonies were isolated 8 days later.

Four replications of this procedure resulted in four variants, designated VM1 through VM4, which exhibited resistance to 5, 10, 25, and 50 µg/mL MPA, respectively, whereas the parental V79 cells were resistant to only 0.1 µg/mL MPA. The increased resistance to MPA cytotoxicity in the variant cells was associated with an increased activity of IMPDH in cell homogenates, with VM1 cells exhibiting about a six-fold increase in IMPDH activity over the parental cells, and VM2, VM3, and VM4 cells expressing about 7-, 9-, and 11-fold increases in IMPDH activity, respectively.

EXAMPLE 2

IMPDH Purification from Chinese Hamster Cells and Human Cells

The generation of the IMPDH overproducing VM2 cell variant in Example 1 facilitated the isolation of a highly purified preparation of IMPDH allowing for the development of a specific anti-IMPDH antibody for subsequent cDNA cloning and immunoblot analysis.

IMPDH was isolated from VM2 Chinese hamster cells as follows. VM2 cells were scraped from the tissue culture plates, and washed with a phosphate buffer saline solution (PBS, pH 7.4, containing 137 mM NaCl, 2.6 mM g/L KCl, 1.5 mM $KH_2PO_4$, and 8 mM $Na_2HPO_4$) containing 0.5 mM phenylmethylsulfonyl fluoride (PMSF). The cells were collected by centrifugation at 800×g for 5 minutes and the pellet homogenized in 10 volumes of buffer A, pH 7.2, which contained 20 mM $KH_2PO_4$, 50 mM KCl, 0.5 mM dithiotreitol (DTT) and 0.1 mM PMSF. The cell homogenate was centrifuged at 180,000×g for 40 minutes at 4° C. The supernatant was removed and applied to a hydroxylapatite column (2.5×30 cm) equilibrated with buffer A. The column was then washed with 10 volumes of buffer A and the protein eluted with a linear gradient of 0–17.5% $(NH_4)_2SO_4$ (400 mL) in buffer A.

IMPDH activity was determined by measuring the IMP-dependent NAD reduction at 37° C. by monitoring the change in absorbance at 340 nm. One unit of enzyme activity was defined as the amount of enzyme forming 1 µmole of NADH per minute at 37° C. under the prescribed assay conditions. Those fractions having enzyme activity were combined and the solution adjusted to 50% saturation with $(NH_4)_2SO_4$. After incubation of this solution at 4° C. for one hour, the precipitate was collected by centrifugation at 12,000×g for 10 minutes. The pellet was dissolved in 50 volumes of buffer B (20 mM Tris-HCl, pH 7.0, 10% glycerol, and 0.5 mM EDTA) and the solution applied to a Blue-Sepharose™ CL-6B column (1.5×20 cm) equilibrated with buffer B. The column was washed with 10 volumes of buffer B followed by 2 volumes of buffer B containing 10 mM NAD and 1 mM IMP. The enzyme was eluted with a linear gradient of 0–1M KCl in 200 mL of buffer B. Fractions with a high specific activity were combined, concentrated by ultrafiltration, and dialyzed against buffer B. The dialyzed material was applied to a DEAE Sepharose™ column (1×5 cm) equilibrated with buffer B. The column was washed with buffer B and the enzyme eluted with a linear KCl gradient (0–0.5 M) in 50 mL of buffer B. Protein concentration was determined by the BCA assay method (Pierce Chemical Co., Rockford, Ill.) with bovine serum albumin used as the standard. The enzyme was purified from a microsomal supernatant to a final specific activity of 1080 mU/mg of protein in a 23% yield.

Polyacrylamide gel electrophoresis was carried out in 7.5% gels as described in Laemmli, *Nature*, 227:680–685 (1970). Upon sodium dodecyl sulfate (SDS) gel electrophoresis, the purified protein migrated as a single species with an apparent molecular weight of 56,000. Two proteins of identical molecular weight were detected by two-dimensional (2D) gel electrophoresis. One of these proteins, constituting less than 10% of the total amount of the protein, is presumably a charge-modified form of the major species. No other proteins were detected when up to one microgram of the purified protein was analyzed by electrophoresis.

Kinetic studies were carried out by varying the substrate conditions. In all cases, linear reciprocal plots were defined by simple regression analysis of the data. The kinetic characteristics of the purified Chinese hamster protein were indistinguishable from those reported for the partially purified enzyme from V79 cells. The $K_m$ values of the Chinese hamster enzyme for IMP and NAD were calculated to be 21 and 29 μM, respectively. Moreover, the Chinese hamster enzyme retained a high sensitivity to MPA with a $K_i$ in the nanomolar range.

IMPDH was partially purified from human HL-60 cells obtained from R.C. Gallo, National Cancer Institute, Bethesda, Md, and were processed as described above with respect to Chinese hamster cells. Comparison of purified Chinese hamster protein with the partially purified human enzyme by 2D-gel electrophoresis indicates these proteins are of a similar molecular weight but that the human enzyme is slightly more acidic than the Chinese hamster enzyme. This observation was later confirmed by a comparison of the deduced amino acid sequences from the human and Chinese hamster cDNA clones (discussed infra), which indicated the human enzyme has one fewer positively charged and one additional negatively charged amino acid.

EXAMPLE 3
Preparation of Rabbit Anti-IMPDH Antiserum, Isolation of IMPDH Specific IgG, and and Development of Assay System An anti-IMPDH antiserum was prepared in rabbits by multiple-site injections of an emulsion of the purified Chinese hamster enzyme, prepared according to Example 2, and Freund's Complete Adjuvant [Vaitukaitis, *Methods Enzymol.*, 73:46–52 (1981)]. IMPDH specific IgG was isolated from the immune serum by Protein A Sepharose™ (Pharmacia Inc., Piscataway, N.J.) chromatography. By immunoblot analysis, this antibody was shown to react with IMPDH isolated from Chinese hamster, rat and human cells.

Assay systems were devised for determination of cellular IMPDH based on use of the rabbit antibody. According to these systems, target cells were washed in PBS and the cell pellet resuspended in 1–5 mL of 20 mM Tris-HCl, pH 6.8, 200 mM KCl, 1 mM DTT (buffer A). The cells were then centrifuged at 12,000×g for 8 seconds and the pellet resuspended in 1.2 mL of buffer A. After three freeze/thaw cycles to disrupt the cells, the suspension was centrifuged at 12,000×g for 10 minutes. The supernatant was removed and 3M NaAc, pH 5.2, was added to give a final concentration of 180 mM. After incubation on ice for 30 minutes, the protein precipitate was recovered by centrifugation for 10 min. in a microfuge. The IMPDH-enriched pellet was resuspended in 0.3 mL of 20 mM Tris-HCl, pH 8.3, 50 mM NaCl, 1 mM DTT. After removal of any insoluble material by centrifugation, aliquots were removed for the determination of enzyme activity and protein content and the remainder of the sample was stored at −20° C.

Western blot analyses [Towbin, et al., *Proc. Nat'l. Acad. Sci. USA*, 76:4350–4354 (1979)] were carried out with the IMPDH-specific IgG prepared from the anti-IMPDH antiserum by Protein A affinity chromatography. The detection level is approximately 1×10$^{-6}$ units of IMPDH, where one unit of enzyme is defined as the amount forming 1 μmol of product per minute at 37° C. under standard assay conditions. The sample is diluted with 5×gel sample buffer (6% SDS; 200 mM DTT; 300 mM Tris-HCl, pH 6.8; 0.25% bromophenol blue; 30% glycerol) and electrophoresed at 50 volts for 12–18 hours. The proteins are transferred to nitrocellulose (Scheicher and Schuell, BA83, 0.2 μm) in 50 mM Tris-HCl, 40 mM glycine, pH 8.3, 15% methanol by application of 100 mamps (20 V) for 8–12 hours. The nitrocellulose blot is incubated in TS (25 mM Tris-HCl, pH 7.5; 150 mM NaCl) with 5% nonfat dry milk for 30 minutes and then with the anti-IMPDH antibody overnight. Immune complexes were visualized by incubation with goat anti-rabbit IgG followed by incubation with rabbit IgG conjugated with horseradish peroxidase and 4-chlornapthol (3 mg/mL in 20% methanol with 0.01% H$_2$O$_2$), used as the substrate. [Kittler, et al., *Anal. Biochem.*, 137:210–216 (1984)].

EXAMPLE 4
Isolation and Characterization of IMPDH cDNA from Mouse Bone Marrow, Chinese Hamster, and Human cDNA Libraries The rabbit antiserum prepared according to Example 3 from the purified Chinese hamster protein was used to screen a λgt11 cDNA expression library derived from mouse bone marrow [Clonetech Laboratories, Inc. (Palo Alto, Calif.)], by means of the screening procedure outlined by Huynh, et al., *DNA Cloning* (Glover, D. M., ed.) 1:73–75 (1985) IRL Press Limited, Washington, D.C. The nitrocellulose filters containing the absorbed phage proteins were incubated in TS (25 mM Tris-HCl, pH 7.5; 150 mM NaCl) with 5% nonfat dry milk for 30 minutes and then with the anti-IMPDH antibody overnight. Immune complexes were visualized as described in Example 3, supra.

A phage with a 750 bp cDNA insert was isolated from this library and the insert subsequently subcloned into a pUC8 vector designated pUC8/IMPDH5. Confirmation of this cDNA probe as having IMPDH coding sequences was obtained by translational arrest as described in Collart, et al., *Mol. Cell. Biol.*, 7:3328–3331 (1987). This technique indicates the extent to which the hybridization of a cDNA probe with putatively homologous mRNA can specifically reduce the yield of the translation product. Poly(A)$^+$RNA isolated from the VM2 cells was used as a source for IMPDH mRNA. The pUC8/IMPDH5 probe effectively blocked the translation of an immunoprecipitable IMPDH product in a dose-dependent manner, thus validating the identity of the clone as a cDNA probe for IMPDH.

A Chinese hamster cDNA library (a generous gift from Victor Ling, University of Toronto, Toronto, Canada) was prepared from a CHO cell line E29Pro+ (Elliott, et al., *Mol. Cell. Biol.*, 5:236–241 (1985); library construction was with the pCD vector system in *E. coli* x1776 [Okayama, et al., *Mol. Cell. Biol.*, 2:161–170 (1982); Okayama, et al., *Mol. Cell. Biol.*, 3:280–289 (1983)]. A human peripheral blood leukocyte cDNA library was purchased from Clonetech Laboratories, Inc. (Palo Alto, Calif.). Both libraries were screened with the mouse IMPDH cDNA probe by using the procedure outlined by Maniatis, et al., "Molecular Cloning", Ch. 10, pages 315–317 and 320–321; Fritsch, F. T., and Sambrook, J., eds.; (Cold Spring Harbor, N.Y. 1982).

The nitrocellulose membranes containing the recombinant DNA were prehybridized for 2 hours at 65° C. in a phosphate buffer, pH 7.2, containing 0.5 M Na$_2$PO$_4$, 1 M NaCl, 1 mM EDTA, 0.5% SDS and 100 μg/mL denatured sonicated salmon sperm DNA. The prehybridization solution was replaced with hybridization solution (prehybridization solution minus the DNA) containing 1×10$^6$ cpm/mL of $^{32}$P-labeled mouse probe, prepared as described by Feinberg, A. P., et al., *Anal. Biochem.*, 132:6–13 (1983), and the membranes incubated at 65° C. for 36 hours. The membranes were washed 3 times for 30 min. in 10 mM NaH$_2$PO$_4$, pH 7.4, 1 mM EDTA, 180 mM NaCl at 50° C. The membranes were dried, sealed in plastic wrap and exposed to x-ray film (Fuji RX) with an intensifying screen (Dupont Cronex "Lightning Plus") at −70° C.

Positive plaques were purified and the phage DNA isolated. Inserts of recombinant IMPDH clones were excised from the positive clones with Eco R1 restriction enzyme and isolated by an electro-elution technique as described by Zassenhaus, et al., *Anal. Biochem.*, 125:125–130 (1982). Insert homogeneity was verified by gel electrophoresis and the concentration determined by measuring the absorbance at 260 nm.

The cloned mouse, human and Chinese hamster IMPDH DNAs were inserted into an M13 vector [Messing, J., *Methods Enzymol.*, 101:20–78 (1983)] and were sequenced according to the dideoxy method [Sanger, F., et al., *Proc. Nat'l. Acad. Sci. USA*, 74:5463–5467 (1977)]. Each nucleotide sequence was read an average of four times and a minimum of once in each direction. Sequence data were compiled and analyzed by the use of the DNASTAR (Madison, Wisc.) system digitizer and software and the accompanying protocols.

As illustrated in FIGS. 1A, 1B, 1C and 1D the largest human cDNA clone, designated HIMP, has 1642 base pairs and contains an open reading frame corresponding to a protein of 514 amino acids with a calculated molecular weight of 56,282. A consensus poly(A) addition site (AATAAA) is located approximately 30 nucleotides from the termination codon at nucleotides 1584–1586. The sequence preceeding the ATG methionine initiation codon at position 48 is consistent with the eukaryotic initiation site consensus sequence described by Kozak, *Nucleic Acids Res.*, 12:857–872 (1984). Plasmid HIMP, containing the cloned human DNA sequence as an EcoRI insert ligated into the EcoRI site of a Bluescript KS+ vector (Stratagene, LaJolla, Calif.) and transformed into *E. coli* DH-1 cells was deposited on Jul. 29, 1988 with the American Type Culture Collection, Rockville, Md. under A.T.C.C. accession No. 67753.

As illustrated in FIGS. 2A, 2B, 2C, and 2D the organization of the Chinese hamster cDNA is similar to that of the human clone and specifies a protein identical in size to the human protein, and contains the poly(A) and ATG concensus sequences.

The mouse DNA fragment was sequenced from both the 5'- end (FIG. 3A) and the 3'- end (FIGS. 3B and 3C). These sequences comprise 737 of the 750 nucleotide base pairs comprising the mouse cDNA. The mouse cDNA sequence (s) display a high degree of similarity to the human cDNA sequence and correspond(s) to the region spanned by nucleotides 405–1157 of the human HIMP clone.

FIGS. 4A and 4B provide a comparison of the deduced amino acid sequences of the human and Chinese hamster proteins and indicates a high level of conservation of the amino acid sequence information. The non-matching amino acids are surrounded by a box with those having similar chemical properties denoted by an asterisk. Of the 514 amino acids specified by the two open reading frames, only eight amino acid differences are noted between the human and the Chinese hamster proteins. Futhermore, five out of eight of these amino acid changes are conservative with respect to the chemical nature of the amino acid. This similarity in amino acid sequence is mirrored in the DNA sequences that show an 89% identity.

Similar results are also obtained from a comparison of the sequence information derived from the mouse IMPDH cDNA, set forth in FIGS. 3A, 3B and 3C, and that derived from the human cDNA, set forth in FIGS. 1A, 1B, 1C, and 1D, wherein a 89% identity was observed. These results confirm the identity of the human, Chinese hamster, and mouse clones as those for IMPDH and demonstrate the high conservation of the amino acid sequence of the enzyme among these three species. In contrast, a comparison was made between the deduced amino acid sequence of the cloned human IMPDH cDNA with all sequences in the NBRF database by using the software provided by the University of Wisconsin Genetics Computer Group [Devereux, et al., *Nuc. Acids. Res.*, 12:387–395 (1984)]. A degree of homology (score 347, 57% similarity over a stretch of 506 amino acids) was observed for the bacterial IMPDH protein. Three regions of 50 amino acids in the interior of the protein sequence show a 56–67% identity in amino acid sequence. If allowance is made for amino acids of similar chemical nature, the similarity of these three regions is approximately 78%.

The similarity of the human, mouse, and Chinese hamster proteins indicates a functional selection for conservation of amino acid sequence. The dissimilarities between eukaryotic and prokaryotic amino acid sequences are indicative of a substantial lack of homology of DNA sequence.

EXAMPLE 5

Protease Digestion and Amino Terminal Sequencing of Purified Chinese Hamster IMPDH Protein Initial attempts to sequence the purified Chinese hamster IMPDH protein indicated that the amino terminus was blocked. In an attempt to further verify the identity of clones putatively coding for the IMPDH protein obtained in Example 4, a portion of the Chinese hamster protein purified according to Example 2 was subjected to protease digestion and amino acid sequencing as follows.

A sample of the purified Chinese hamster protein in 20 mM Tris-HCl, pH 8.0, 200 mM KCl, 10 mM DTT, and 0.25% SDS was heated at 65° C. for 2 minutes. *Staphlococcus aureus* V-8 protease was added at a weight/weight ratio of protease to substrate of 1:100, and the solution was incubated at 37° C. for two hours. The sample was then chilled to 0° C. and centrifuged at 12,000×q for two minutes. The resulting peptides in the supernatant were purified by reversed-phase high-pressure liquid chromatography on a Synchropack C4 column (4.1×100 mm). Small aliquots (50 μL) containing approximately 350 pmoles of digested enzyme were loaded to minimize the effects of SDS. The peptides were eluted with a linear gradient (0–100%) of 60/39/1:acetonitrile/water/trifluoreacetic acid. Flow rate was 1 mL/min with a gradient duration of 30 minutes. Peptide peaks were collected in microfuge tubes, lyophilized, and stored at −70° C. Amino terminal sequencing was performed at the Chicago Medical School, North Chicago, Ill., by using an Applied Biosystems (Foster City, Calif.) protein sequencer, amino acid analyzer, and the accompanying protocols.

A sequence of 35 amino acids obtained by analysis of one of the peptides was compared with the protein sequence deduced from the human and Chinese hamster cDNA clones. This 35 amino acid segment, indicated by a box in FIG. 1C, corresponds to deduced amino acid residues 336–370 in both the human and Chinese hamster proteins.

EXAMPLE 6

The Preparation and Use of an IMPDH DNA Construct as a Selectable Marker

This example describes the preparation and use of IMPDH DNA constructs, which permit identification of cells that have incorporated a selective fragment of foreign DNA into their genetic material. The successful practice of the procedures is based on the requirement of IMPDH as a normal constituent of the cell for cell survival and the knowledge that inhibitors of IMPDH can be cytotoxic to cells at concentrations of 0.1 to 0.5 μg/mL. Increased cellular levels of IMPDH confer resistance to IMPDH inhibitors and negate the cytotoxic effects of these agents.

DNA sequences that can be readily combined with the IMPDH DNA sequence include any DNA desired sequences that can be ligated into the plasmid construct and that will not compromise the ability of the IMPDH cDNA product to specify resistance to MPA (myophenolic acid) or to other IMPDH inhibitors. The constructs can be incorporated into cells by using standard DNA transfection technology (Davis, et al., *Molecular Biology*, 18–1:286–289; Davis, L. G., et al., eds. Science Publishing Co., Inc.; Elsevier, N.Y. 1986). After transfection, the addition of an IMPDH inhibitor to the culture medium will permit the growth of only those cells that have incorporated the construct into their genetic material. Cells that have not acquired the construct will be killed by the IMPDH inhibitor.

DNA sequences coding for the IMPDH enzyme were ligated into the pMSG plasmid (Pharmacia, Inc., Piscataway, N.J.), which contains appropriate expression sequences and the DNA sequence coding for the *E. coli* gpt protein. A SMAI-EcoRV fragment derived from the HIMP plasmid was subcloned into the SMAI site of the pMSG plasmid. This process placed the IMPDH cDNA under the control of a dexametasone-inducible mouse mammary tumor virus promoter. This plasmid construct was then introduced into V15 hamster cells (derived by mutagen treatment of Chinese hamster V79 cells and having no detectable HGPRT activity) by using the calcium phosphate DNA transfection technique described in Davis, et al., *Molecular Biology*, 18–1:286–289 (1986), supra.

After introduction of the construct into the hamster cells, mycophenolic acid (2 μg/mL) was added to the culture medium to select for those cells that had integrated the construct into their genetic material. Those cells that have integrated the construct into their genetic material produce the IMPDH enzyme and are therefore resistant to the cytotoxic effects of mycophenolic acid. A cell clone designated IMP1 was isolated; this clone was resistant to mycophenolic acid, indicating that the cells had incorporated the construct and were over-producing the IMPDH enzyme.

To verify that the resistance resulted from the incorporation of the construct, the MPA-resistant cells were successfully transferred to HAT medium. [Dulbecco's modified MEM containing 5% fetal bovine serum, aminopterin (2 μg/mL), and mycophenolic acid (25 μg/mL), and supplemented with hypoxanthine (15 μg/mL), thymidine (10 μg/mL), and xanthine (250 μg/mL)]. The ability of the cells to grow in the selective medium is attributable to the production of the *E. coli* gpt enzyme, which catalyzes the production of xanthine monophosphate from the reaction of xanthine and phosphoribosyl pyroposphate. Presence of the enzyme compensates for the purine de novo synthetic block imposed by the presence of aminopterin and MPA. The dual resistance to mycophenolic acid and HAT selection displayed by the transformed host is evidence that the resistance is attributable to the incorporation of DNA of the plasmid construct. Growth of the cells for several generations in the absence of mycophenolic acid did not decrease the resistance of the cell clone to MPA, indicating that the construct DNA was incorporated into host chromosomal material.

The IMPDH expression in the IMP1 cell clone and the V15 parent was examined to further define the basis for the mycophenolic acid resistance. A five-fold increase in the IMPDH activity in cell homogenates was observed in the IMP1 cells relative to the V15 parent. The cellular protein in these cell homogenates was electrophoresed through polyacrylamide gels, transferred to nitrocellulose and the amount of IMPDH enzyme was quantitated by immunoblot analysis with the anti-IMPDH antiserum prepared according to Example 3. In-both the V15 and IMP1 cells, the antiserum reacted with a protein of 56 kDa corresponding to IMPDH. The amount of IMPDH enzyme was approximately five-fold higher in the IMP1 cells than in the V15 parent. Furthermore, the relative gel migration distance of the two proteins was identical, suggesting the IMPDH protein produced in the IMP1 cells has the same molecular weight as the V15 enzyme.

The amount of IMPDH mRNA in the parent and transformed cell lines was quantitated by Northern blot analysis by using a human IMPDH cDNA probe, prepared according to Example 4. Total cellular RNA was isolated by disrupting cells in guanidinium lysis buffer, pH 7.0, composed of 4 M guanidinium thiocyanate, 50 mM potassium acetate, 0.1 M β-mercaptoethanol, and 0.5% sarcosyl. The RNA was purified by centrifugation through a CsCl cushion as described by Chrigwin, et al., *Biochemistry*, 18:5294–5299 (1979). Hybridization signals corresponding to a 2.2 kilobase message were detected in both the IMP1 and V15 cells. However, the IMP1 cells contained an additional hybridization band corresponding to a message size of approximately 2.0 kilobases. This is the approximate message size expected for transcription of IMPDH mRNA from the plasmid construct. These results show that the IMP1 cells overproduce an IMPDH enzyme that is indistinguishable, by polyacrylamide gel electrophoresis, from that produced by V15 cells, and suggest that the increased IMPDH is a result of transcription from the plasmid construct containing the human IMPDH cDNA.

The foregoing example demonstrates that the selectable marker system of the invention provides a convenient means to study and obtain a regulated expression of virtually any selected foreign DNA. Moreover IMPDH is a dominant marker and no requirement for use of deficient hosts exists.

EXAMPLE 7

Analysis of IMPDH Expression in Normal and Malignant Cells

To determine whether increased amounts of IMPDH mRNA are the cause of the elevated levels of IMPDH in tumor cells, total cellular RNA from a variety of growing human leukemic cell lines and in normal peripheral blood granulocytes and lymphocytes was examined by Northern blot analysis through the use of the human cDNA as described in Example 6.

The human promyelocytic HL-60 leukemia cells were supplied by R. Gallo (National Cancer Institute, Bethesda, Md.). Cells were grown in Dulbecco's modified Eagle's medium or RPMI 1640 medium supplemented with 10% fetal calf serum, penicillin (100 U/mL), streptomycin (100 μg/mL), fungizone (0.25 μg/mL), and glutamine (2 mM) in a humidified incubator supplied with a constant amount of 8% $CO_2$ in air. Peripheral blood leukocytes were isolated from freshly drawn peripheral blood by Histoplaque-1077 (Sigma Chemical Co., St. Louis, Mo.) gradient centrifugation as described in Boyum, A., *Scand. J. Clin. Lab. Invest.*, 21(97):51–55 (1968); and Klock, J. C., and Bainton, D. F., *Blood*, 48:149–161 (1976). The mononuclear fraction contained predominately lymphocytes (85–95%), with monocytes comprising the remaining percentage. Immediately after purification, the lymphocytes were resuspended in appropriate buffers for either Western blot analysis or for isolation of total cellular RNA.

A reduced level of IMPDH expression was consistently observed for the RNA isolated from lymphocytes relative to the leukemic cell lines that had markedly increased expression of a 2.2 kb transcript corresponding to the IMPDH message. A similar pattern was observed for the amounts of cellular IMPDH detected with the specific IMPDH antibody in conjunction with the Western blotting technique. These results were similar in that much higher amounts of the IMPDH protein were observed in the leukemic cells relative to the peripheral blood cells. Similar results were also obtained for measurements of the enzyme activity in these cell lines. These marked differences in the expression, amount, and activity, between the normal and leukemic cells may be associated with the absence of cell replication in the normal cells and the active proliferation of the leukemic cells.

Cultured normal human fibroblast and sarcoma cells were similarly analyzed. The differences in IMPDH expression between the normal and tumor cells were not as great as those observed between the leukemic cells and the normal peripheral blood cells. However, all of the sarcoma cells had higher levels of mRNA expression, larger amounts of the protein, and greater IMPDH activity than the normal fibroblasts. These differences may again be attributable in part to a difference in the growth rate of the various cell types because the 37-h doubling time of the normal fibroblasts is greater than that observed for the sarcoma cells. However, other factors appear to influence the IMPDH expression because an absolute correlation between IMPDH activity and cellular growth rate was not always observed for the tumor cell lines.

The foregoing illustrative examples relate, in part, to the isolation of cDNA sequences encoding mouse, Chinese hamster, and human species IMPDH proteins. Those skilled in the art will readily appreciate that the DNA and deduced amino acid sequence information provided herein make available numerous other forms of DNA sequences, such as genomic sequences obtainable by hybridization screening of genomic libraries through the use of DNA probes designed by using the sequence information of FIG. 1A, FIG. 1B, FIG. 1C, FIG. 1D, FIG. 2A, FIG. 2B, FIG. 2C, FIG. 2D, FIG. 3A, FIG. 3B, and FIG. 3C, or manufactured DNA sequences synthesized from nucleic acids and potentially including alternate (degenerate) codons specifying the same amino acids, or DNA sequences comprising, e.g., part cDNA and part manufactured DNA. In a like manner, the DNA sequence information provided herein enables the isolation of other eukaryotic DNAs encoding IMPDH such as avian (chicken, turkey), fish, and mammalian (bovine, ovine, porcine) species DNAs by means of hybridization screening under appropriate stringency conditions.

The availability of the above-noted DNA sequences allows for preparation of IMPDH by in vitro transcription and translation of the DNA and for the development of a wide variety of viral or circular plasmid DNA vectors useful both for the biological amplification of the DNA and for the securing of recombinant expression of the DNA of proteins having IMPDH biological activities in prokaryotic and, especially, eukaryotic, host cells and organisms.

Well-known recombinant means for introducing genes into host cells and organisms have been described. For example, Palmiter, et al., *Science*, 222:809 (1983), have described transgenic mice containing the human growth hormone gene fused to a promoter sequence. Maclean, N., et al., *Bio/Tech.*, 5:257 (1987), have produced transgenic fish. Caplan, A., et al., *Science*, 222:815–821 (1983), described the use of a modified plasmid for use as a vector to transfer foreign genes into plants. More recently, Sinkar, V. P., et al., *Genes & Development*, 2:688–697 (1988), described transgenic tobacco plants. These recombinant means are expected to allow for the production of plant or animal organisms into which IMPDH encoding DNA has been introduced and which therefore contain increased endogenous levels of guanosine-5'-monophosphate (GMP). GMP, a natural constituent of all living materials and normally present only in trace amounts, is a member of a family of flavor potentiators commonly used as food additives. GMP enhances the taste intensity of certain flavors and can suppress the perception of a sour or bitter taste. [Heath, et al., "Flavor Chemistry and Technology", AVI Publishing Co., Westport, Conn., (1986)]. When combined with the commonly used food additive, monosodium glutamate, GMP acts synergistically to enhance flavor and it is therefore possible to enhance the taste properties of certain foods by increasing the endogeneous GMP levels. Organisms with increased levels of GMP can also provide a ready source for the isolation and extraction of GMP for use as a food additive. Studies of tissue culture cells with altered levels of IMPDH activity show an association between increased IMPDH activity and elevated GMP levels. [Ullman, *J. Biol. Chem.*, 258:523–528 (1983)]. Thus, selection for an organism with increased levels of IMPDH activity simultaneously selects for organisms with elevated tissue levels of GMP.

Microinjection and other transformation techniques are expected to readily allow for incorporation of extra copies of IMPDH encoding DNA into host cells and organisms, with exposure of the cells and organisms to inhibitors such as MPA providing a basis for selection of those cells having incorporated the desired sequences.

Cells and organisms having enhanced IMPDH production levels are, of course, also made available according to the present invention by means of the screening and selection procedures applied in Example 1. Briefly, a selected somatic or embryonic cell type is (either with or without prior exposure to mutagenic influences) screened in culture for the capacity to survive in the presence of elevated levels of an inhibitor such as MPA. Cells capable of surviving in the screening environment, e.g., at levels of MPA of 0.5 to 1.0 $\mu$L/mL, are thereafter subjected to stepwise incremental selection at much higher levels of the inhibitor. The resulting cells and organisms having enhanced IMPDH synthetic capacity vis-a-vis parent cells will also be expected to display enhanced capacity for synthesis of GMP.

Among the additional forms of DNA provided by the invention are those that encode allelic variants of the specific mammalian IMPDH protein FIG. 1A, FIG. 1B, FIG. 1C, FIG. 1D, FIG. 2A, FIG. 2B, FIG. 2C, and FIG. 2D, as well as analog proteins that possess one or more variations in IMPDH biological activities.

Protein and peptide products of the invention include not only those produced as recombinant expression products of "full-length" and fragmentary DNA sequences of the invention but also those that are prepared by chemical synthesis from amino acids. As one example, analysis of the deduced amino acid sequences of IMPDH proteins is expected to provide valuable information concerning potential antigenic epitopes present therein, allowing for the preparation of synthetic antigenic peptides duplicative of about 6 to 20 continuous residues of the protein. These, in turn, are expected to allow for the preparation of monospecific polyclonal and monoclonal antibodies useful in the quantitative detection of IMPDH proteins. Further, it is ancipated that the deduced amino acid sequences information can be used to modify existing drugs and to design new drugs as inhibitors of IMPDH activity.

Numerous modifications and variations in the invention as described in the above illustrative examples are expected to occur to those skilled in the art; consequently, only such limitations as appear in the appended claims should be placed thereon.

Accordingly, it is intended in the appended claims to cover all such equivalent variations that come within the scope of the invention as claimed.

What is claimed is:

1. A purified monoclonal antibody that binds to a IMPDH polypeptide, wherein the polypeptide is encoded by a DNA segment comprising a nucleic acid sequence of SEQ ID NO:1, SEQ ID NO:2, SEQ ID NO:3, SEQ ID NO:4, SEQ ID NO:5 or SEQ ID NO:6.

2. The antibody of claim 1, wherein said polypeptide is a mammalian IMPDH.

3. The antibody of claim 2, wherein said mammal is a hamster.

4. The antibody of claim 2, wherein said mammal is a human.

5. The antibody of claim 1, wherein said IMPDH polypeptide is encoded by a DNA segment comprising a nucleic acid sequence of SEQ ID NO:1.

6. The antibody of claim 1, wherein said IMPDH polypeptide is encoded by a DNA segment comprising a nucleic acid sequence of SEQ ID NO:2.

7. The antibody of claim 1, wherein said IMPDH polypeptide is encoded by a DNA segment comprising a nucleic acid sequence of SEQ ID NO:3.

8. The antibody of claim 1, wherein said IMPDH polypeptide is encoded by a DNA segment comprising a nucleic acid sequence of SEQ ID NO:4.

9. The antibody of claim 1, wherein said IMPDH polypeptide is encoded by a DNA segment comprising a nucleic acid sequence of SEQ ID NO:5.

10. The antibody of claim 1, wherein said IMPDH polypeptide is encoded by a DNA segment comprising a nucleic acid sequence of SEQ ID NO:6.

11. A purified monoclonal antibody that binds to a IMPDH polypeptide, wherein the polypeptide comprises an amino acid sequence having at least 20 contiguous amino acids in common with the sequence of SEQ ID NO:7 or SEQ ID NO:8.

12. The antibody of claim 11, wherein the polypeptide comprises an amino acid sequence having at least 20 contiguous amino acids in common with the sequence of SEQ ID NO:7.

13. The antibody of claim 11, wherein the polypeptide comprises an amino acid sequence having at least 20 contiguous amino acids in common with the sequence of SEQ ID NO:8.

* * * * *

UNITED STATES PATENT AND TRADEMARK OFFICE
CERTIFICATE OF CORRECTION

| | |
|---|---|
| PATENT NO. | : 6,147,194 |
| DATED | : November 14, 2000 |
| INVENTOR(S) | : Frank R. Collart and Eliezer Huberman |

It is certified that error appears in the above-identified patent and that said Letters Patent is hereby corrected as shown below:

Column 1,
Line 4, before "This" -- This invention was made with Government support under Contract No. W-31-109-ENG-38 awarded by the Department of Energy. The Government has certain rights in this invention. --

Signed and Sealed this

Sixth Day of November, 2001

Attest:

NICHOLAS P. GODICI
Attesting Officer    Acting Director of the United States Patent and Trademark Office